(12) United States Patent
Lecomte et al.

(10) Patent No.: US 11,446,164 B1
(45) Date of Patent: Sep. 20, 2022

(54) VARIABLE STIFFNESS MECHANISMS

(71) Applicant: Össur Iceland ehf, Reykjavik (IS)

(72) Inventors: Christophe Guy Lecomte, Reykjavik (IS); Felix Starker, Reykjavik (IS)

(73) Assignee: Össur Iceland ehf, Reykjavik (IS)

( * ) Notice: Subject to any disclaimer, the term of this patent is extended or adjusted under 35 U.S.C. 154(b) by 187 days.

(21) Appl. No.: 16/131,769

(22) Filed: Sep. 14, 2018

Related U.S. Application Data

(60) Provisional application No. 62/559,376, filed on Sep. 15, 2017.

(51) Int. Cl.
| | |
|---|---|
| *A61F 2/66* | (2006.01) |
| *F16F 1/368* | (2006.01) |
| *F16F 1/37* | (2006.01) |
| *F16F 3/12* | (2006.01) |
| *F16F 3/093* | (2006.01) |

(Continued)

(52) U.S. Cl.
CPC ............ *A61F 2/66* (2013.01); *F16F 1/20* (2013.01); *F16F 1/368* (2013.01); *F16F 3/0935* (2013.01); *A61F 2002/5006* (2013.01); *A61F 2002/6657* (2013.01); *A61F 2002/6664* (2013.01); *F16F 2224/025* (2013.01); *F16F 2224/0225* (2013.01); *F16F 2224/0241* (2013.01); *F16F 2228/04* (2013.01); *F16F 2228/066* (2013.01);

(Continued)

(58) Field of Classification Search
None
See application file for complete search history.

(56) References Cited

U.S. PATENT DOCUMENTS

| | | |
|---|---|---|
| 25,238 A | 8/1859 | Bly |
| 53,931 A | 4/1866 | Weston et al. |

(Continued)

FOREIGN PATENT DOCUMENTS

| | | |
|---|---|---|
| CA | 2 127 691 | 5/1994 |
| CA | 2 234 362 | 10/1998 |

(Continued)

OTHER PUBLICATIONS

Merlette et al., The Springlite Foot: The Design Process For a Novel Advanced Composite Prosthesis, in "Composites in Manufacturing", published by the Society of Manufacturing Engineers in 1991.*

(Continued)

*Primary Examiner* — David H Willse
(74) *Attorney, Agent, or Firm* — Knobbe, Martens, Olson & Bear, LLP

(57) ABSTRACT

A variable stiffness spring assembly includes first and second members made of a first material and separated by a gap along at least a portion of their lengths, and one or more layers made of a second material disposed in the gap. The variable stiffness spring assembly can be incorporated into or take the form of a limb support assembly, such as a prosthetic foot. The second material disposed between the first and second members is rate-sensitive or speed-dependent, such that the material exhibits different properties when the user of the prosthetic foot is walking at high or fast walking speeds compared to low or slow walking speeds. The prosthetic foot can exhibit high damping and energy absorption, and therefore stability, at slow speeds, and high energy return at faster speeds.

18 Claims, 21 Drawing Sheets

(51) Int. Cl.
*F16F 1/20* (2006.01)
*A61F 2/50* (2006.01)

(52) U.S. Cl.
CPC ..... *F16F 2230/40* (2013.01); *F16F 2238/022* (2013.01)

(56) References Cited

U.S. PATENT DOCUMENTS

| | | | |
|---|---|---|---|
| 56,983 A | 8/1866 | Nicholas | |
| 57,666 A | 9/1866 | Bly | |
| 368,580 A | 8/1887 | Frees | |
| 487,697 A | 12/1892 | Ehle | |
| 534,198 A | 2/1895 | Chapman | |
| 619,731 A | 2/1899 | Doerflinger et al. | |
| 808,296 A | 12/1905 | Merrick | |
| 809,876 A | 1/1906 | Wilkins | |
| 817,340 A | 4/1906 | Rosenkranz | |
| 2,183,076 A | 12/1939 | Kaiser | |
| 2,197,093 A | 4/1940 | Campbell | |
| 2,315,795 A | 4/1943 | Johnson et al. | |
| 2,357,893 A | 9/1944 | Harrington | |
| 2,594,945 A | 4/1952 | Lucas et al. | |
| 2,692,392 A | 10/1954 | Bennington et al. | |
| 2,731,645 A | 1/1956 | Woodall | |
| 3,551,914 A | 1/1971 | Woodall | |
| 3,784,988 A | 1/1974 | Trumpler | |
| 3,874,004 A | 4/1975 | May | |
| 4,007,497 A | 2/1977 | Haupt | |
| 4,360,931 A | 11/1982 | Hampton | |
| 4,387,472 A | 6/1983 | Wilson | |
| 4,547,913 A | 10/1985 | Phillips | |
| 4,636,220 A | 1/1987 | Ziegelmeyer | |
| 4,718,913 A | 1/1988 | Voisin | |
| 4,822,363 A | 4/1989 | Phillips | |
| 4,892,553 A | 1/1990 | Prahl | |
| 4,892,554 A | 1/1990 | Robinson | |
| 4,959,073 A | 9/1990 | Merlette | |
| 5,019,109 A | 5/1991 | Voisin | |
| 5,037,444 A | 8/1991 | Phillips | |
| 5,062,859 A | 11/1991 | Naeder | |
| 5,112,356 A | 5/1992 | Harris et al. | |
| 5,116,384 A | 5/1992 | Wilson et al. | |
| 5,139,525 A | 8/1992 | Kristinsson | |
| 5,156,631 A | 10/1992 | Merlette | |
| 5,181,932 A | 1/1993 | Phillips | |
| 5,181,933 A | 1/1993 | Phillips | |
| 5,219,365 A | 6/1993 | Sabolich | |
| 5,258,039 A | 11/1993 | Goh et al. | |
| 5,290,319 A | 3/1994 | Phillips | |
| 5,376,133 A | 12/1994 | Gramnaes | |
| 5,376,141 A | 12/1994 | Phillips | |
| 5,387,246 A | 2/1995 | Phillips | |
| 5,443,527 A | 8/1995 | Wilson | |
| 5,443,529 A | 8/1995 | Phillips | |
| 5,509,938 A | 4/1996 | Phillips | |
| 5,545,234 A | 8/1996 | Collier, Jr. | |
| 5,571,210 A | 11/1996 | Lindh | |
| 5,653,767 A | 8/1997 | Allen et al. | |
| 5,701,686 A * | 12/1997 | Herr | A43B 5/06 36/27 |
| 5,728,177 A | 3/1998 | Phillips | |
| 5,800,589 A | 9/1998 | Phillips | |
| 5,888,239 A | 3/1999 | Wellershaus et al. | |
| 5,897,594 A | 4/1999 | Martin et al. | |
| 5,899,944 A | 5/1999 | Phillips | |
| 5,913,901 A | 6/1999 | Lacroix | |
| 5,941,913 A | 8/1999 | Woolnough et al. | |
| 5,957,981 A | 9/1999 | Gramnaes | |
| 5,993,488 A | 11/1999 | Phillips | |
| 6,071,313 A | 6/2000 | Phillips | |
| 6,099,572 A | 8/2000 | Mosler et al. | |
| 6,129,766 A | 10/2000 | Johnson et al. | |
| 6,165,227 A | 12/2000 | Phillips | |
| 6,206,934 B1 | 3/2001 | Phillips | |
| 6,241,776 B1 | 6/2001 | Christensen | |
| 6,261,324 B1 | 7/2001 | Merlette | |
| 6,280,479 B1 | 8/2001 | Phillips | |
| 6,350,286 B1 | 2/2002 | Atkinson et al. | |
| 6,387,134 B1 | 5/2002 | Parker et al. | |
| 6,398,818 B1 | 6/2002 | Merlette et al. | |
| 6,402,790 B1 | 6/2002 | Celebi | |
| 6,443,993 B1 | 9/2002 | Koniuk | |
| 6,443,995 B1 | 9/2002 | Townsend et al. | |
| 6,562,075 B2 | 5/2003 | Townsend et al. | |
| 6,596,029 B1 | 7/2003 | Gramnäs | |
| 6,663,673 B2 | 12/2003 | Christensen | |
| 6,712,860 B2 | 3/2004 | Rubie et al. | |
| 6,719,807 B2 | 4/2004 | Harris | |
| 6,767,370 B1 | 7/2004 | Mosler et al. | |
| 6,793,683 B1 | 9/2004 | Laghi | |
| 6,855,170 B2 | 2/2005 | Gramnäs | |
| 6,899,737 B1 | 5/2005 | Phillips | |
| 6,942,704 B2 | 9/2005 | Sulprizio | |
| 6,969,408 B2 | 11/2005 | Lecomte et al. | |
| 7,029,500 B2 | 4/2006 | Martin | |
| 7,052,519 B1 | 5/2006 | Gramnäs | |
| 7,341,603 B2 | 3/2008 | Christensen | |
| 7,347,877 B2 | 3/2008 | Clausen et al. | |
| 7,507,259 B2 | 3/2009 | Townsend et al. | |
| 7,520,904 B2 | 4/2009 | Christensen | |
| 7,578,852 B2 | 8/2009 | Townsend et al. | |
| 7,727,285 B2 | 6/2010 | Christensen et al. | |
| 7,763,082 B1 | 7/2010 | Curtis | |
| 7,766,974 B2 | 8/2010 | Curtis | |
| 7,862,622 B2 | 1/2011 | Dunlap et al. | |
| 7,942,935 B2 | 5/2011 | Iversen et al. | |
| 8,007,544 B2 | 8/2011 | Jonsson et al. | |
| 8,025,699 B2 | 9/2011 | Lecomte et al. | |
| 8,246,695 B2 | 8/2012 | Mosler | |
| 8,317,876 B2 | 11/2012 | Mosler | |
| 8,377,144 B2 | 2/2013 | Jonsson et al. | |
| 8,574,313 B2 | 11/2013 | Clausen et al. | |
| 8,764,850 B2 | 7/2014 | Hanset et al. | |
| 8,814,949 B2 | 8/2014 | Gramnaes | |
| 8,888,864 B2 | 11/2014 | Iversen et al. | |
| 8,915,969 B2 | 12/2014 | Boender | |
| 9,366,306 B2 | 6/2016 | Miyasato et al. | |
| 9,427,338 B2 | 8/2016 | Clausen et al. | |
| 9,968,467 B2 | 5/2018 | Jonsson et al. | |
| 10,821,007 B2 | 11/2020 | Albertsson et al. | |
| 10,980,648 B1 | 4/2021 | Lecomte et al. | |
| 2002/0013628 A1 | 1/2002 | Harris | |
| 2002/0040249 A1 | 4/2002 | Phillips | |
| 2002/0087216 A1 | 7/2002 | Atkinson et al. | |
| 2002/0116072 A1 | 8/2002 | Rubie et al. | |
| 2002/0143408 A1 | 10/2002 | Townsend et al. | |
| 2002/0183860 A1 | 12/2002 | Wilkinson | |
| 2003/0093158 A1 | 5/2003 | Phillips et al. | |
| 2003/0120353 A1 | 6/2003 | Christensen | |
| 2004/0064195 A1 | 4/2004 | Herr | |
| 2004/0068327 A1 | 4/2004 | Christensen | |
| 2004/0122529 A1 | 6/2004 | Townsend et al. | |
| 2004/0162623 A1 | 8/2004 | Phillips | |
| 2004/0181289 A1 | 9/2004 | Bédard et al. | |
| 2004/0225376 A1 | 11/2004 | Townsend et al. | |
| 2005/0038524 A1 | 2/2005 | Jonsson et al. | |
| 2005/0038525 A1 | 2/2005 | Doddroe et al. | |
| 2005/0107889 A1 | 5/2005 | Bédard et al. | |
| 2005/0137717 A1 | 6/2005 | Gramnaes | |
| 2005/0267603 A1 | 12/2005 | Lecomte et al. | |
| 2005/0273179 A1 | 12/2005 | Townsend et al. | |
| 2006/0069450 A1 | 3/2006 | McCarvill et al. | |
| 2006/0235545 A1 | 10/2006 | Habecker | |
| 2007/0027557 A1 | 2/2007 | Jonsson et al. | |
| 2007/0250178 A1 | 10/2007 | Wilson | |
| 2009/0204229 A1 | 8/2009 | Mosley et al. | |
| 2009/0222105 A1 | 9/2009 | Clausen | |
| 2013/0218297 A1 | 8/2013 | Nordman, Jr. et al. | |
| 2014/0249652 A1 | 9/2014 | Taszreak | |
| 2015/0257902 A1 | 9/2015 | Martin | |
| 2015/0328020 A1 | 11/2015 | Clausen et al. | |
| 2015/0351938 A1 | 12/2015 | Moser et al. | |
| 2016/0008147 A1 * | 1/2016 | Marlin | A61F 2/6607 623/55 |

(56) References Cited

U.S. PATENT DOCUMENTS

| | | |
|---|---|---|
| 2016/0033053 A1 | 2/2016 | Battlogg et al. |
| 2016/0310298 A1 | 10/2016 | Jonsson et al. |
| 2017/0049584 A1 | 2/2017 | Pusch et al. |
| 2017/0051808 A1* | 2/2017 | Bogrash ............... B60G 11/00 |
| 2017/0128236 A1 | 5/2017 | Meyer et al. |
| 2018/0153712 A1 | 6/2018 | Albertsson et al. |
| 2021/0077281 A1 | 3/2021 | Albertsson et al. |

FOREIGN PATENT DOCUMENTS

| | | |
|---|---|---|
| CN | 1196917 | 10/1998 |
| DE | 817 186 | 10/1951 |
| DE | 834 884 | 3/1952 |
| DE | 832 473 | 4/1952 |
| DE | 838 480 | 5/1952 |
| DE | 924 230 | 2/1955 |
| DE | 1 491 182 | 7/1969 |
| DE | 1 941 762 | 3/1971 |
| DE | 22 41 971 | 3/1974 |
| DE | 298 20 904 | 4/1999 |
| DE | 200 15 175 | 12/2000 |
| EP | 0 401 864 | 9/1989 |
| EP | 0 940 129 | 11/1992 |
| EP | 0 648 479 | 4/1995 |
| EP | 1 149 568 | 10/2001 |
| EP | 2 944 290 | 11/2015 |
| FR | 661 071 | 7/1929 |
| FR | 1 213 026 | 3/1960 |
| FR | 2 658 717 | 8/1991 |
| GB | 117547 | 8/1918 |
| GB | 120462 | 11/1918 |
| GB | 621576 | 4/1949 |
| GB | 625528 | 6/1949 |
| GB | 1 371 996 | 10/1974 |
| KR | 2000-0000930 | 1/2000 |
| KR | 2000-0002059 | 1/2000 |
| KR | 2000-0047310 | 7/2000 |
| KR | 2001-0055393 | 7/2001 |
| KR | 2002-0041137 | 6/2002 |
| SE | 9400380-3 | 8/1995 |
| SU | 1454449 | 1/1989 |
| SU | 1600759 | 10/1990 |
| SU | 1700759 | 12/1991 |
| WO | WO 88/006431 | 9/1988 |
| WO | WO 93/004645 | 3/1993 |
| WO | WO 94/018914 | 9/1994 |
| WO | WO 96/004869 | 2/1996 |
| WO | WO 98/053769 | 12/1998 |
| WO | WO 99/052476 | 10/1999 |
| WO | WO 00/027317 | 5/2000 |
| WO | WO 01/006965 | 2/2001 |
| WO | WO 02/002034 | 1/2002 |
| WO | WO 02/051342 | 7/2002 |
| WO | WO 2004/032809 | 4/2004 |
| WO | WO 2005/048887 | 6/2005 |
| WO | WO 2011/066354 | 6/2011 |
| WO | WO 2017/077541 A1 * | 5/2017 ............... F16F 1/22 |

OTHER PUBLICATIONS

Burden et al., "Numerical Analysis", Second Edition, Review of Calculus, Section 1.1, 1981, Prindle, Weber & Schmidt, p. 3.

Commercial Ad for College Park Venture Prosthetic Foot; http://www.college-park.com/assets/pdf/VentureInfoSheets.pdf, © 2003, and www.college-park.com/CPStore/ProductInfoVenture.asp; available before Aug. 15, 2003 in 4 pages.

Freedom Innovations FS2000 LP product; https://www.freedom-innovations.com/product_details.asp?seriesid=1&prodid=2, © 2003; available before Aug. 15, 2003, 1 page.

Freedom Innovations Runway Product; http://www.freedom-innovations.com/product_details.asp?seriesid=2&prodid=11, © 2004; available before Dec. 18, 2003 in 1 page.

Ohio Willow Wood Company: Carbon Copy System III brochure available before May 2004, 5 pages.

ÖSSUR Allurion product; http://www.ossur.com/template1.asp?pageid=84 and product catalog pp. 146-149; available before Aug. 15, 2003 in 5 Total pages.

ÖSSUR Elation product; http://www.ossur.com/template1.asp?pageid=263 and product catalog pp. 193-196; available before Aug. 15, 2003.

ÖSSUR Total Concept Product, ÖSSUR Products Catalog, 2001-2002, pp. 243-249.

Otto Bock—Axtion product; http://www.ottobockus.com/products/lower_limb_prosthetics/axtion.asp; believed to have been released May 2004.

The Quantum Foot (Hosmer Dorrance Corporation), Circa 1988, 4 pages.

The Quantum Foot Brochure (Technical Information), Early 1989, 6 pages.

* cited by examiner

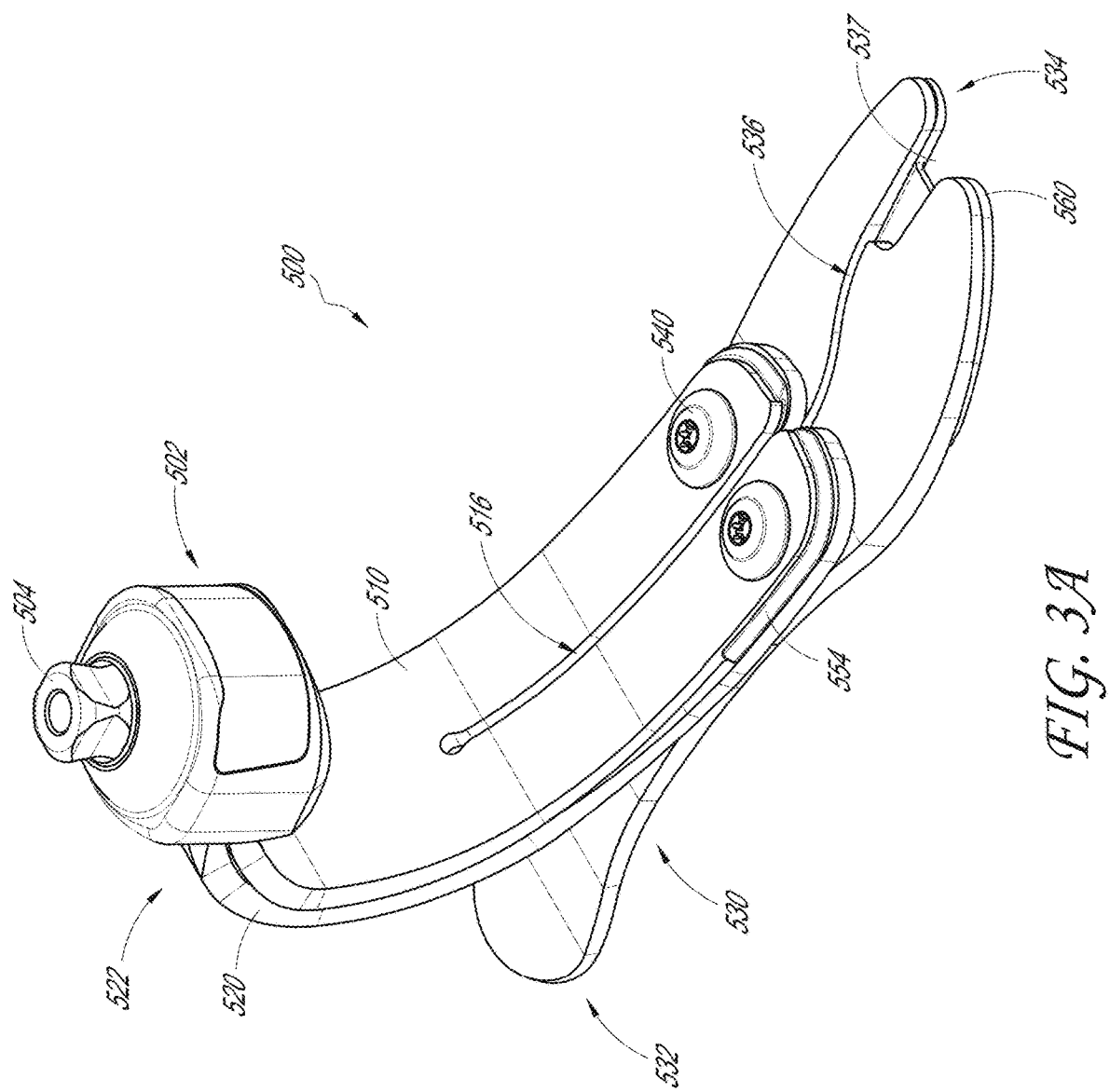

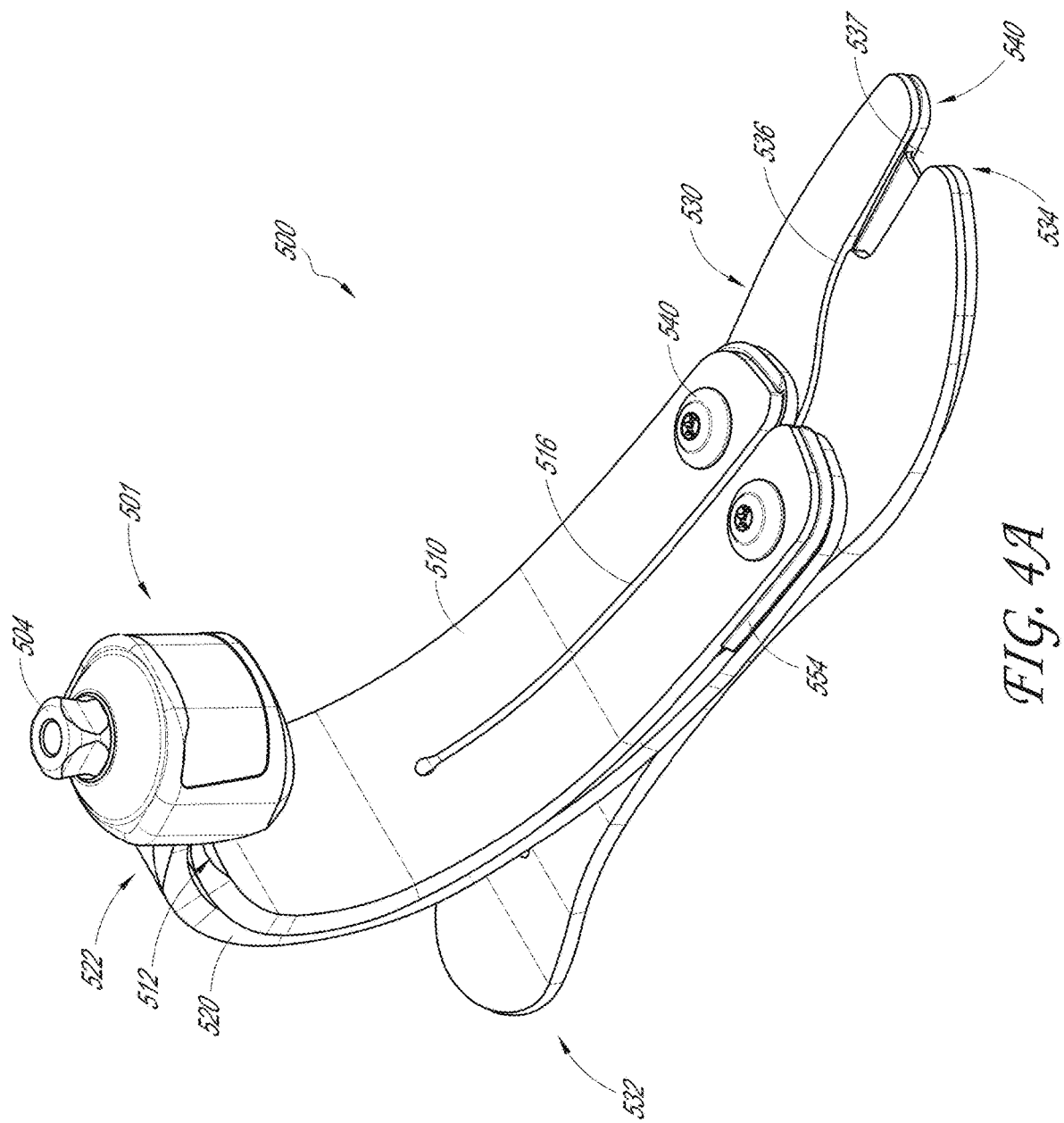

VARIABLE STIFFNESS MECHANISMS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 62/559,376, filed Sep. 15, 2017, the entirety of which is incorporated herein by reference and should be considered a part of this specification.

BACKGROUND

Field

The present application relates to spring assemblies including variable stiffness mechanisms. Such assemblies and mechanisms can be used for example, in prosthetic feet and other prosthetic or orthotic devices.

Description of the Related Art

In the field of prosthetics, particularly prosthetic feet, it is desirable to provide a high level of functionality with reliable performance. Some existing passive prosthetic feet are made of low energy returning materials such as wood or polyurethane foams. Such feet do not provide significant energy return at higher or faster walking speeds and do not allow for an energy efficient gait pattern. Some existing passive prosthetic feet are made of higher energy returning materials such as carbon fiber. Such feet can provide a greater energy return, closer to an ideal spring, which can allow a more energy efficient gait at higher walking speeds, for example, greater than around 3 km/h. However, such high energy return feet may provide more limited stability at slower walking speeds, for example, less than around 3 km/h. Some existing electronically controlled and actuated prosthetic feet are able to vary the ankle joint angle of the prosthetic foot and generate a net positive energy push-off force during use. However, such feet are more complex and may have increased weight compared to passive prosthetic feet due to the energy source and actuator.

SUMMARY

In some embodiments, a spring assembly includes a first elongate member extending along a length and made of a first material; a second elongate member extending generally parallel to the first elongate member along a length and made of the first material, the second elongate member separated from the first elongate member by a gap along at least a portion of its length; and one or more layers of a time-dependent second material disposed in the gap.

The second material can be a non-Newtonian material. The second material can be an open or closed cell polyurethane. The first material can be carbon fiber. The second material can act in one or both of compression and extension. The second material can act in compression and extension independent with different characteristics for extension vs. compression. Stiff characteristics of the second material can adjust automatically in compression and extension. The one or more layers can have a wave shape configured to increase compression ratios of the one or more layers. The second material can act in a shear direction relative to one or both of the first and second elongate members. The one or more layers can be fixed at first and second ends of the one or more layers via bonding or clamping. The one or more layers can be bonded to one or both of the first and second ends. The one or more layers can extend partially along a length of the gap. The one or more layers can extend along substantially an entire length of the gap. The spring assembly can comprise a limb support assembly. The limb support assembly can comprise a prosthetic foot.

In some embodiments, a prosthetic foot includes a first elongate member extending along a length and made of a first material; a second elongate member extending generally parallel to the first elongate member along a length and made of the first material, the second elongate member separated from the first elongate member by a gap along at least a portion of its length; and one or more layers of a time-dependent second material disposed in the gap. The prosthetic foot exhibits greater energy absorption and damping at slower gait speeds and greater energy return and stiffer spring characteristics at faster gait speeds.

The slower gait speeds can be less than about 3 km/h. The faster gait speeds can be greater than about 5 km/h. A storage modulus G' of the second material can decrease from the slower gait speeds to the faster gait speeds.

The second material can be a non-Newtonian material. The second material can be an open or closed cell polyurethane. The first material can be carbon fiber. The second material can act in one or both of compression and extension. Stiff characteristics of the second material can adjust automatically in compression and extension. The second material can act in compression and extension independent with different characteristics for extension vs. compression. The one or more layers can have a wave shape configured to increase compression ratios of the one or more layers. The second material can act in a shear direction relative to one or both of the first and second elongate members. The one or more layers can be fixed at first and second ends of the one or more layers via bonding or clamping. The one or more layers can be bonded to one or both of the first and second ends. The one or more layers can extend partially along a length of the gap. The one or more layers extend along substantially an entire length of the gap.

BRIEF DESCRIPTION OF THE DRAWINGS

These and other features, aspects, and advantages of the invention disclosed herein are described below with reference to the drawings of preferred embodiments, which are intended to illustrate and not to limit the invention. Additionally, from figure to figure, the same reference numerals have been used to designate the same components of an illustrated embodiment. The following is a brief description of each of the drawings.

FIG. 3A is a perspective view of another example embodiment of a prosthetic foot including a material having variable stiffness properties disposed between distal portions of two foot elements.

FIG. 4A is a perspective view of another example embodiment of a prosthetic foot including a material having variable stiffness properties disposed between distal portions of two foot elements.

DETAILED DESCRIPTION

The present disclosure relates to spring assemblies including one or more layers of a first material disposed between two spring members made of a second material different from the first material, or made of one or more materials different from the first material. The first material can be a speed dependent or rate sensitive material, where the stiffness of the material can vary based on speed (e.g., rate of compression and/or shear rate of the material). Such spring assemblies can be made or incorporated into, for example, prosthetic feet or other prosthetic or orthotic or limb support devices. In such an embodiment, the second material can optionally be carbon fiber. Such a configuration can provide a passive prosthetic foot with variable stiffness that self-adjusts based on the user's gait speed due to the material properties of the speed dependent material. Such a passive prosthetic foot advantageously does not require components such as batteries, sensors, processors or actuators, which can increase the weight of a prosthetic foot and make the prosthetic foot more complex or vulnerable to certain malfunctions.

A natural human foot and/or ankle varies its stiffness based on the activity being performed by the user, such as walking at various speeds, rising to stand from a seated position, ascending and descending stairs, walking on uneven terrain, and/or running. The foot can vary between, for example, relatively low stiffness and relatively high damping during slow walking, which can allow for easier transitions, and relatively higher stiffness and relatively lower damping when walking at faster speeds, which can provide greater energy efficiency. Some currently available prosthetic feet are adapted for either high damping, e.g., via hydraulic mechanism, or high energy efficiency, e.g., via carbon fiber leaf springs. However, such prosthetic feet typically have fixed damping and/or spring characteristics optimized for a particular gait speed on level ground and may not adapt well to other speeds or activities. Prosthetic feet made of composites are tuned for minimal energy loss and generally don't provide any time dependent stiffness changes during use. While materials such as rubber and polyurethane used in damping elements in a prosthetic foot may provide some time-dependent damping based on the material characteristics, the effect of any such time-dependent damping is small and does not provide sufficient variation in stiffness to adapt well to various speeds of ambulation with such a prosthetic foot.

The prosthetic feet described herein include variable stiffness mechanisms and/or properties. Such mechanisms can allow the foot to continuously fade or adapt between relatively high damping with relatively low stiffness and low rebound and relatively low damping with relatively high stiffness and a high rebound.

Figure 1:
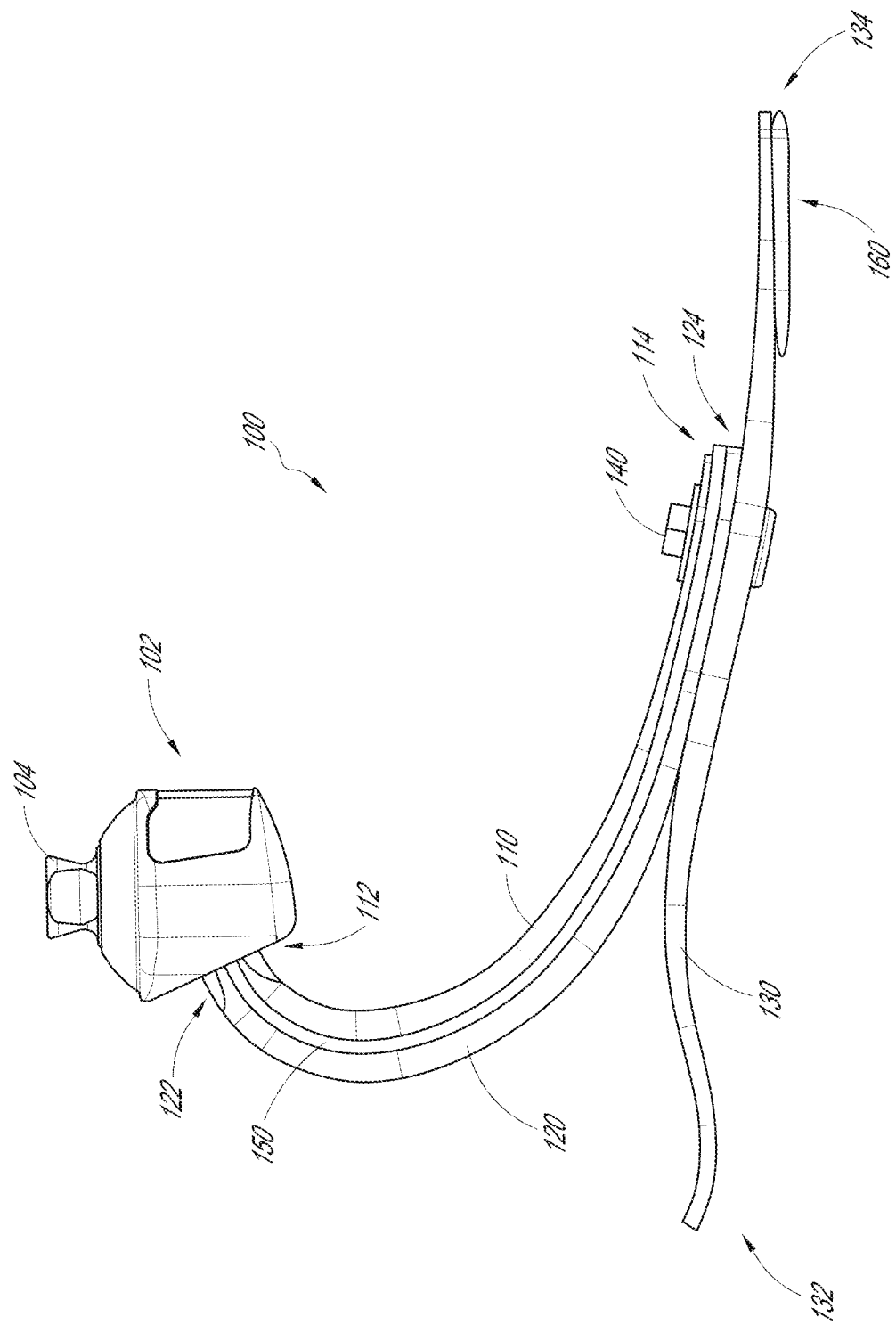
FIG. 1 is a side view of an example embodiment of a prosthetic foot including a material having variable stiffness properties disposed between two foot elements.

FIG. 1 shows an example embodiment of a spring assembly according to the present disclosure in the form of a prosthetic foot 100. FIGS. 2A-2D shows an example embodiment of a spring assembly according to the present disclosure in the form of a prosthetic foot 100'. The prosthetic foot 100, 100' can include an adapter 102 including an attachment member 104, such as a pyramid connector as shown, to couple prosthetic foot 100, 100' to the user's residual limb or another prosthetic component (e.g., socket, pylon, etc.).

In the embodiment of FIGS. 1 and 2A-2D, the prosthetic foot 100, 100' includes dual upper foot elements 110, 120 and a lower foot element 130. The foot elements 110, 120, 130 are made of a resilient, energy storing material, such as carbon fiber. The upper foot elements 110, 120 extend generally parallel to each other (e.g., along their entire lengths) and have generally the same shape. In the illustrated embodiment, the upper foot elements 110, 120 are generally C-shaped. Other shapes are also possible (e.g., J-shape). The upper foot elements 110, 120 are separated by a gap along at least a portion of their lengths (e.g., along their entire lengths). Proximal ends 112, 122 of the upper foot elements 110, 120 can be coupled to each other and/or coupled (separately) to and/or received in the adapter 102. In the illustrated embodiment, the lower foot element 130 extends from a proximal end 132 that forms a heel end of the prosthetic foot 100, 100' to a distal end 134 that forms a toe end of the prosthetic foot 100, 100'. The upper foot elements 110, 120 extend from their proximal ends 112, 122 to distal ends 114, 124 located proximal to the distal end 134 of the lower foot element 130. In other words, the upper foot elements 110, 120 do not extend to the toe end of the prosthetic foot 100, 100'.

The upper foot elements 110, 120 and lower foot element 130 can be coupled via fasteners 140, such as bolts, and/or an adhesive material. In some embodiments, the foot elements 110, 120, 130 can be loosely connected via fasteners through elongate holes on the foot elements 110, 120, 130 so that the foot elements can flex more than when the foot elements are connected via generally round holes. In the illustrated embodiment, the upper foot elements 110, 120 and lower foot element 130 are coupled proximate the distal ends of the upper foot elements 110, 120. Other configurations are also possible. For example, one or both of the upper foot elements 110, 120 can extend to the toe end of the prosthetic foot 100, 100'. The lower foot element 130 can extend from the heel end of the prosthetic foot 100, 100' to a distal end 134 that is proximal to the toe end of the prosthetic foot 100, 100'. The lower foot element 130 may form a heel member that does not extend the full length of the prosthetic foot, and one or both of the upper foot elements 110, 120 may extend beyond the distal end 134 of the lower foot element 130 to define the toe end of the prosthetic foot 100, 100'. In some embodiments, any of the foot elements can include a slit that extends longitudinally along at least a portion of the foot element to at least partially separate the foot element into medial and lateral blades that can flex at least partially independently.

Figure 2A:
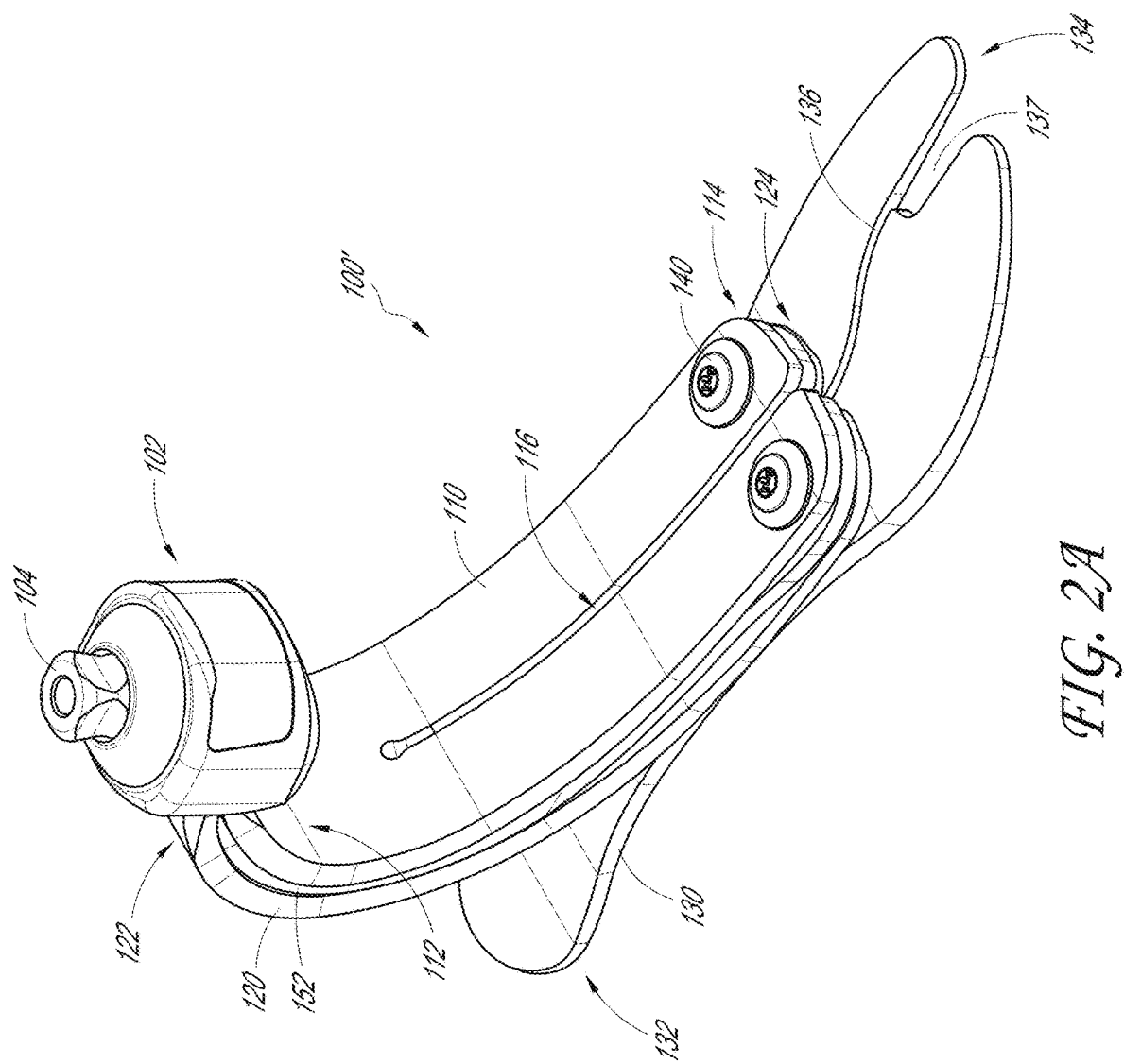
FIG. 2A is a perspective view of another example embodiment of a prosthetic foot including a material having variable stiffness properties disposed between two foot elements.
Figure 2B:
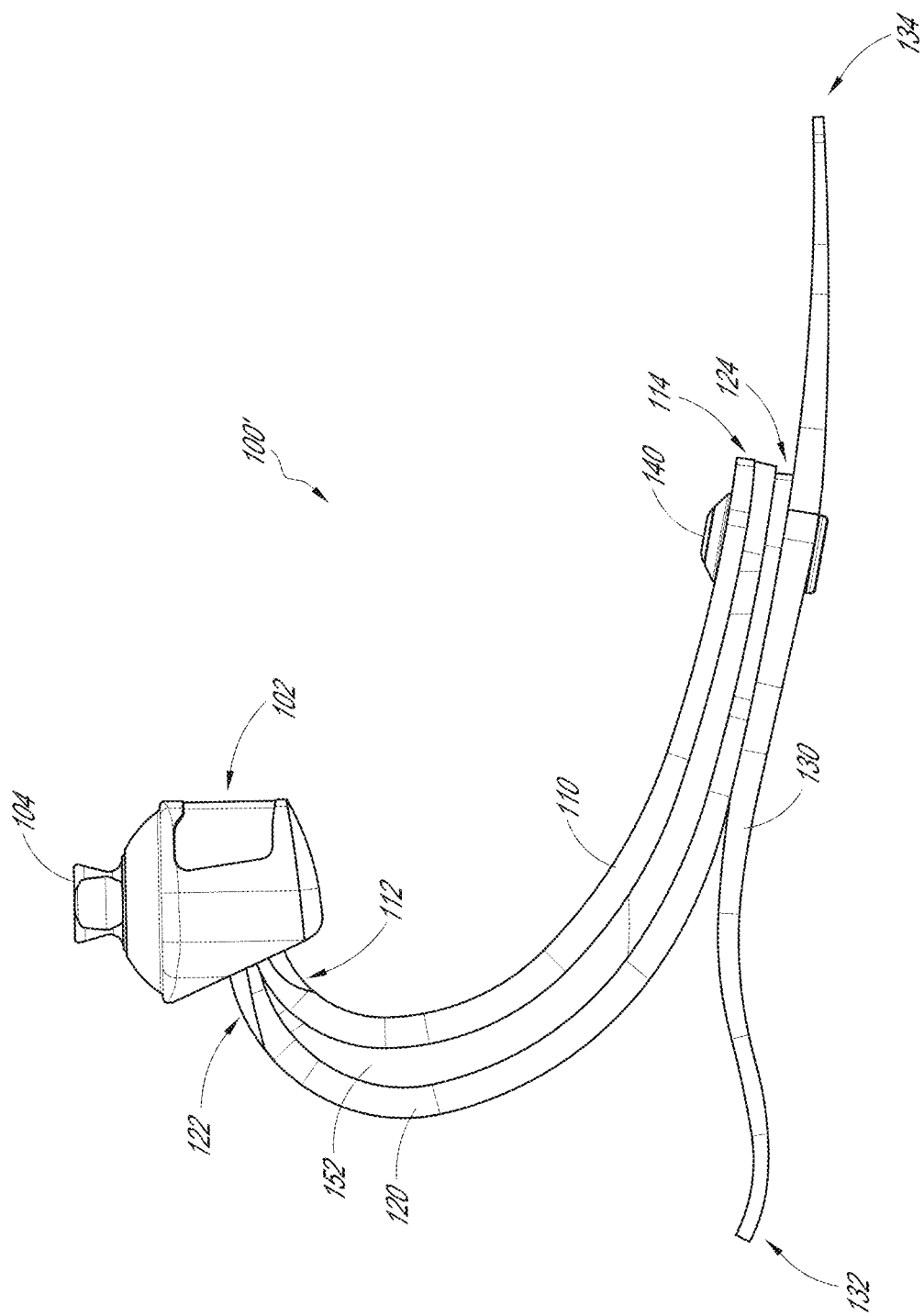
FIG. 2B is a side view of the prosthetic foot of FIG. 2A.

The gap between the upper foot elements 110, 120 can be at least partially filled with one or more layers 150 of a material that has variable stiffness properties, thereby providing variable stiffness properties to the prosthetic foot 100, 100'. As shown in FIGS. 1 and 2A-2B, the gap between the upper foot elements 110, 120 is filled along substantially an entire length of the gap with one or more layers 150 (FIG. 1), 152 (FIGS. 2A-2B, 2E) of a material that provides variable stiffness properties. As shown in FIG. 2E, the one or more layers 152 can include openings 157 near its distal end for accommodating the fasteners 140 therethrough. The layers 150 can have a similar structure and/or shape. In some embodiments, the layers 150 and the layers 152 may differ in one or more dimensions (e.g., thickness). A proximal end of the one or more layers 150 can have a taper to fit into a proximal end of the gap between the upper foot elements 110, 120. The material can be speed-dependent or rate-sensitive such that the material properties vary with or adapt to different gait speeds of the user in use. The layers 150 of material with variable stiffness automatically adjust in stiffness during use. Such different gait speeds can result in different rates of compression of the one or more layers 150, 152 of the material, and the material can exhibit different stiffness properties based on the different rates of compression. The material can be, for example, a non-Newtonian material, an open or closed cell polyurethane foam, or another suitable polymer. An example of a material that can be used is a material sold by D3O Lab in United Kingdom. In some embodiments, the material can optionally be an electro-active polymer or piezo-electric material, which can allow for active control and variation of the stiffness. However, such embodiments may require a power source and associated additional weight. In some embodiments, the one or more layers 150, 152 can include or be made of different materials, arranged in series or in parallel.

Figure 2C:
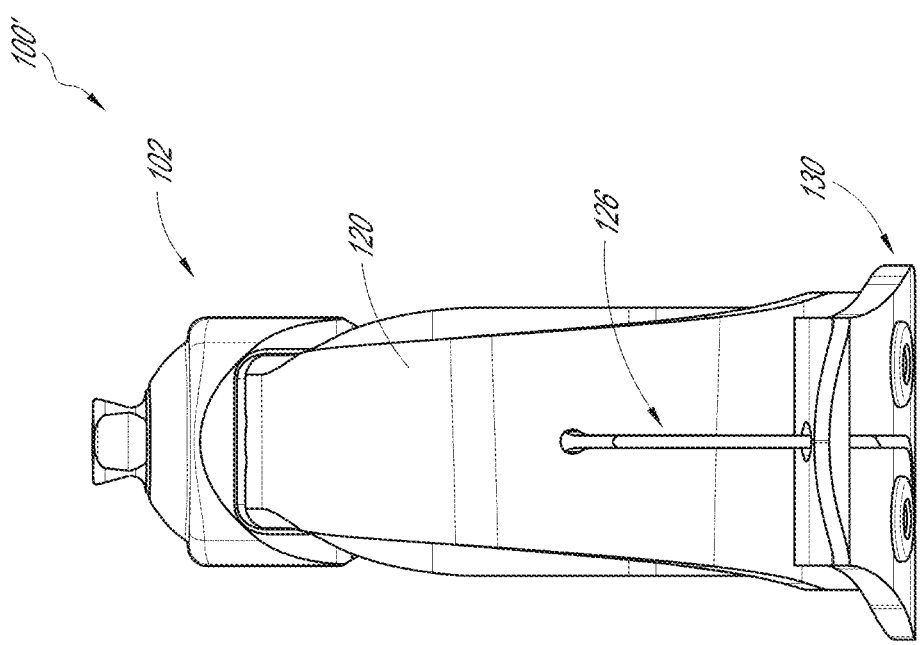
FIG. 2C is a rear view of the prosthetic foot of FIG. 2A.
Figure 2D:
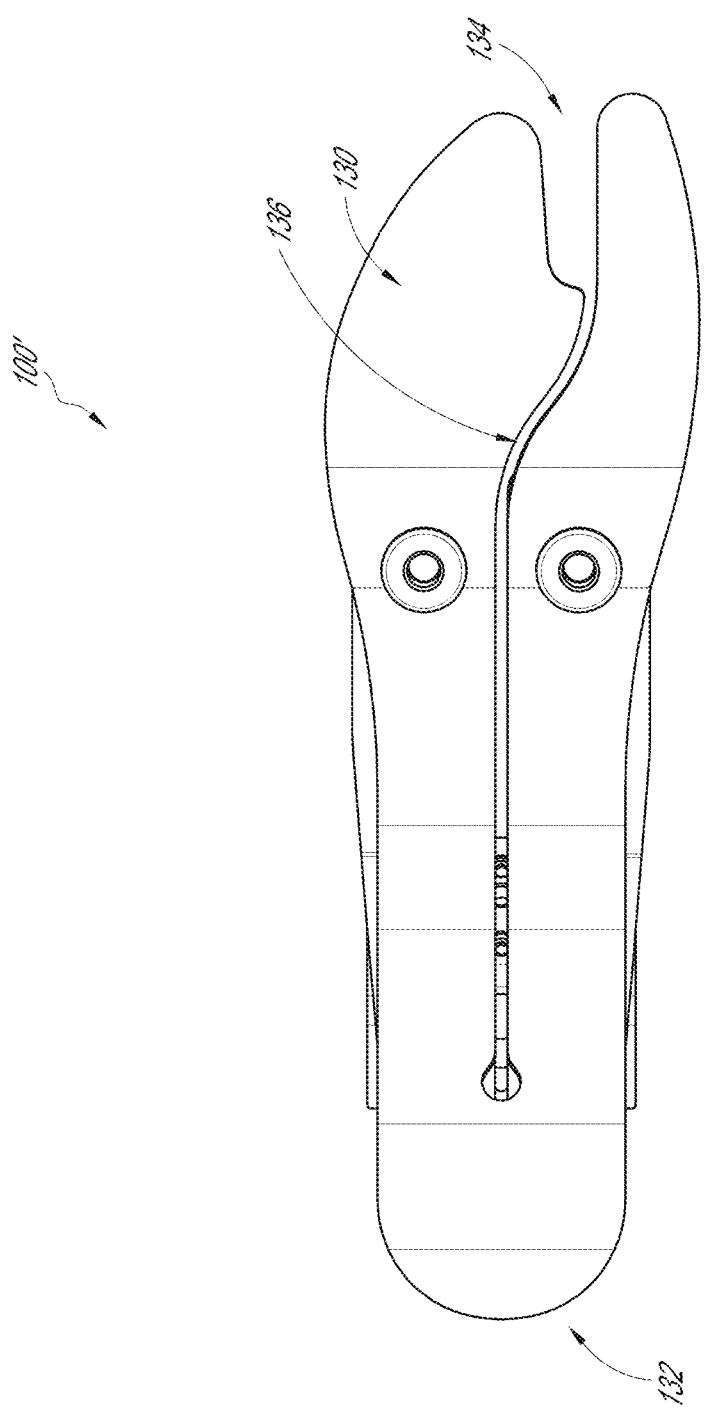
FIG. 2D is a bottom view of the prosthetic foot of FIG. 2A.
Figure 2E:
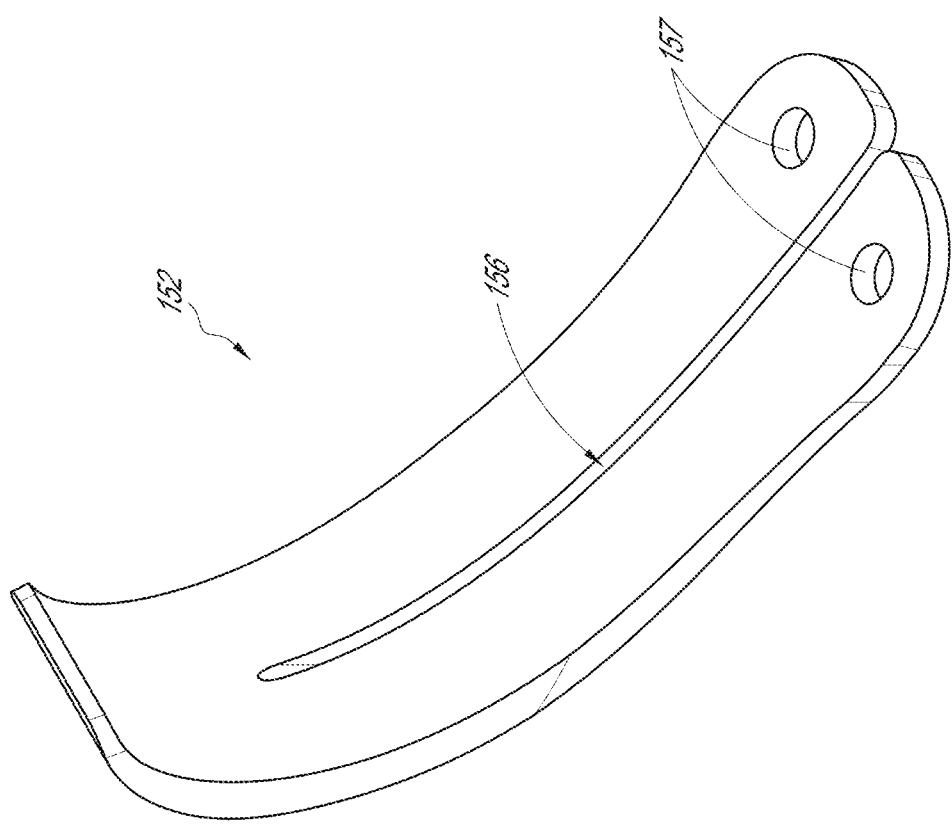
FIG. 2E is a perspective view of the material having variable stiffness properties in FIG. 2A.

As shown in FIGS. 2A, 2C and 2D, the lower foot element 130 can include a lengthwise split 136, extending along at least part of the length of the lower foot element 130. In the illustrated embodiment, the split 136 begins at a point spaced from (or distal to) the proximal end 132 of the lower foot element 130 and extends to the toe end 134 of the lower foot element 130. The lengthwise split 136 can divide the lower foot element 130 into a medial portion and a lateral portion. The split 136 can bend medially and extend to a generally U-shaped gap 137 between the medial portion and lateral portions. The lateral portion can be wider than the medial portion at the distal or toe region of the lower foot element 130. The upper foot elements 110, 120 can also include a lengthwise split 116, 126. As shown in FIG. 2E, the one or more layers 152 can also include a corresponding split 156. The splits 116, 126 in the upper foot elements 110, 120 and the split 156 in the one or more layers 152 can substantially align and allow the medial and lateral portions of the lower foot element 130 to flex at least somewhat independently, improving functional properties of the prosthetic foot during rollover or during use on different surfaces (e.g., on uneven terrain).

Figure 3B:
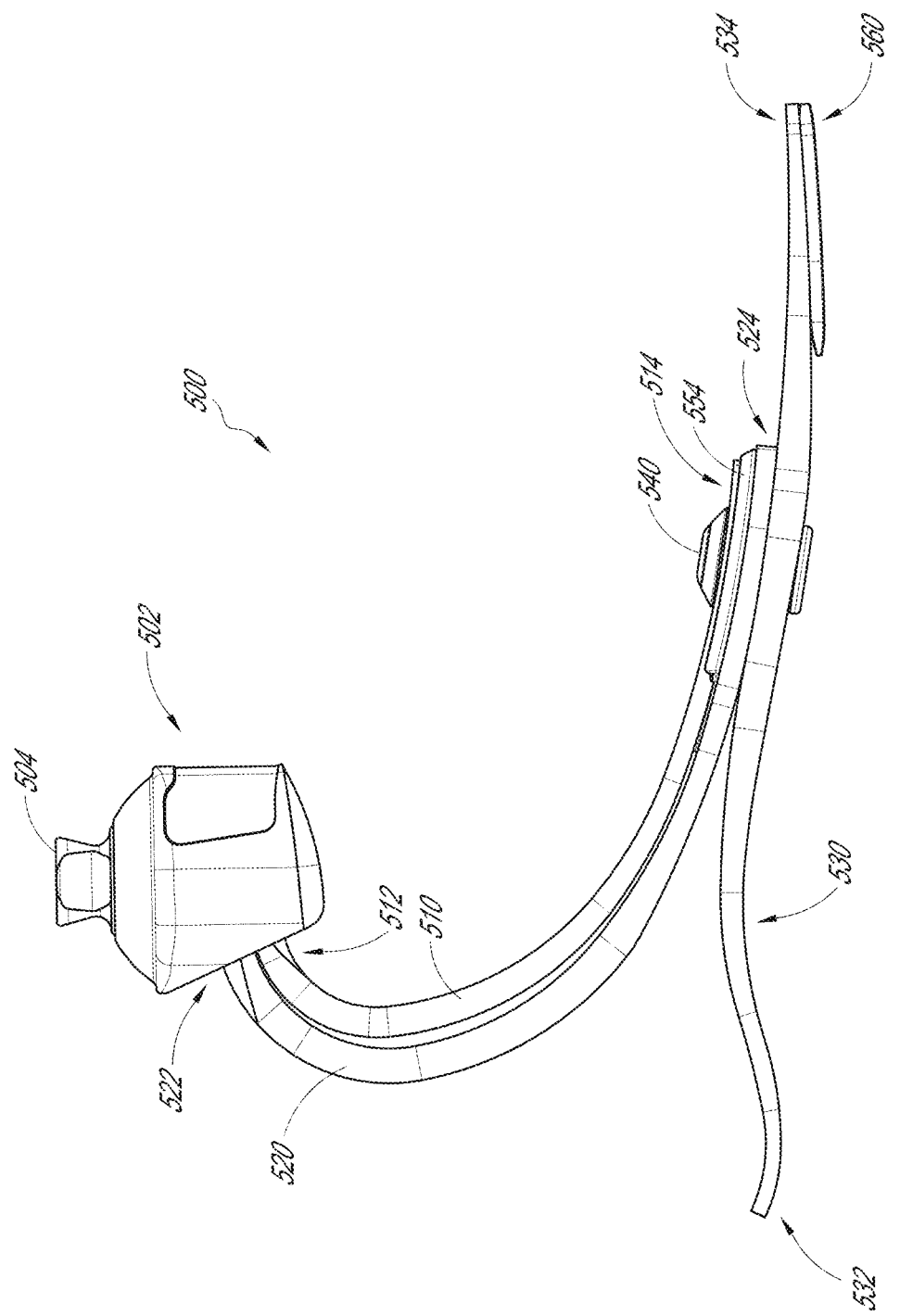
FIG. 3B is a side view of the prosthetic foot of FIG. 3A.
Figure 3C:
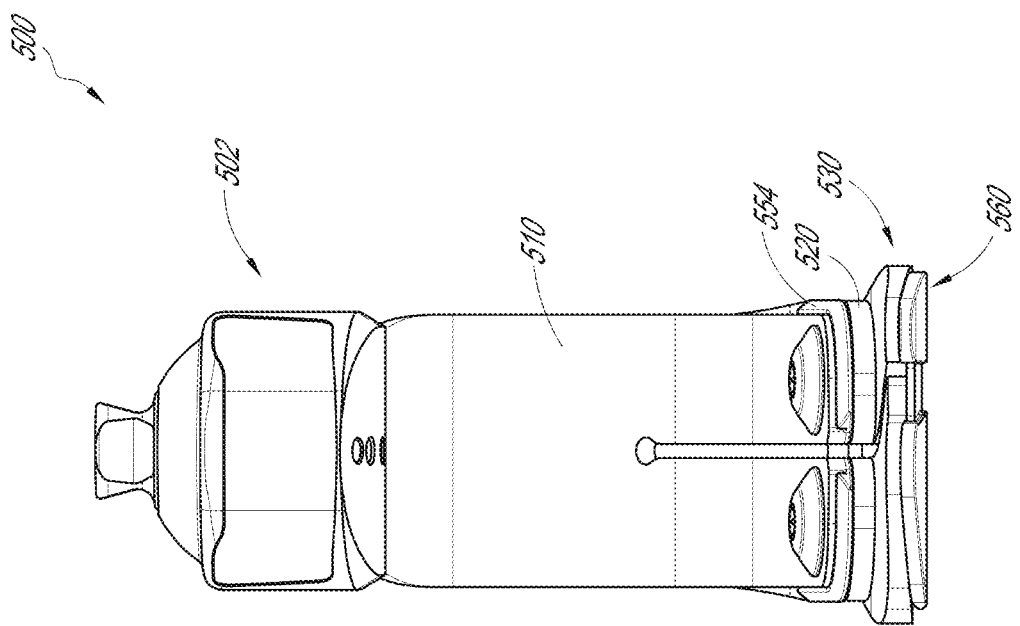
FIG. 3C is a front view of the prosthetic foot of FIG. 3A.
Figure 3D:
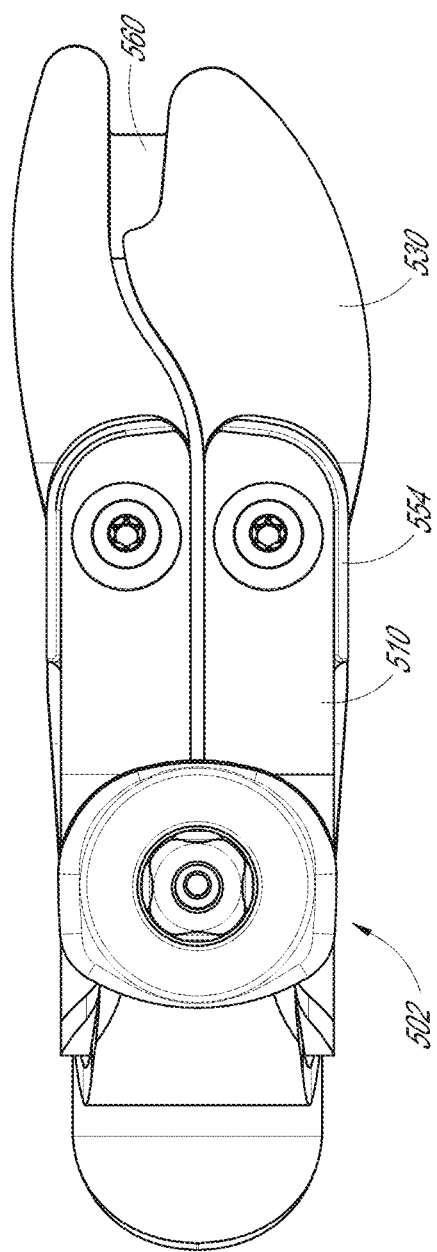
FIG. 3D is a top view of the prosthetic foot of FIG. 3A.
Figure 3E:
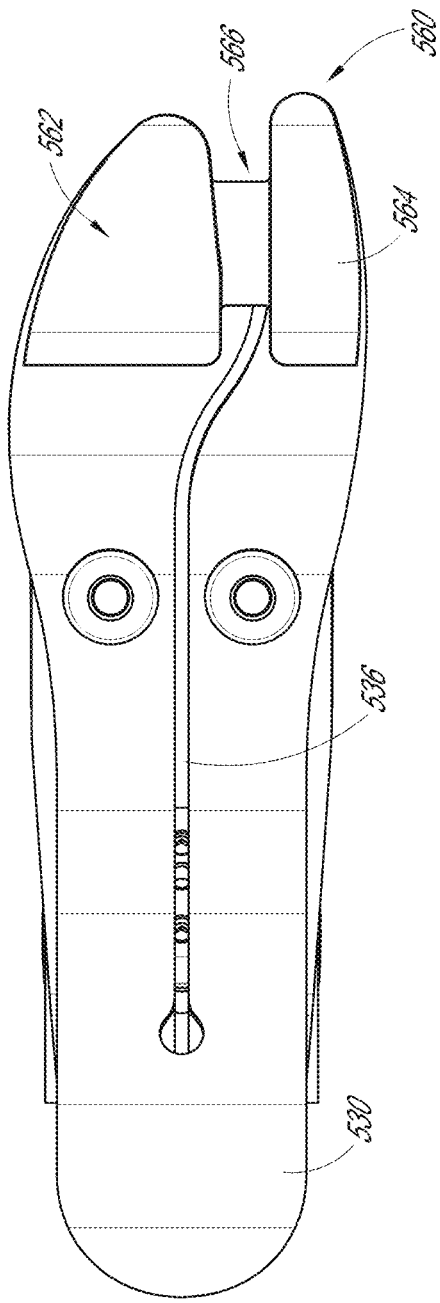
FIG. 3E is a bottom view of the prosthetic foot of FIG. 3A.
Figure 4B:
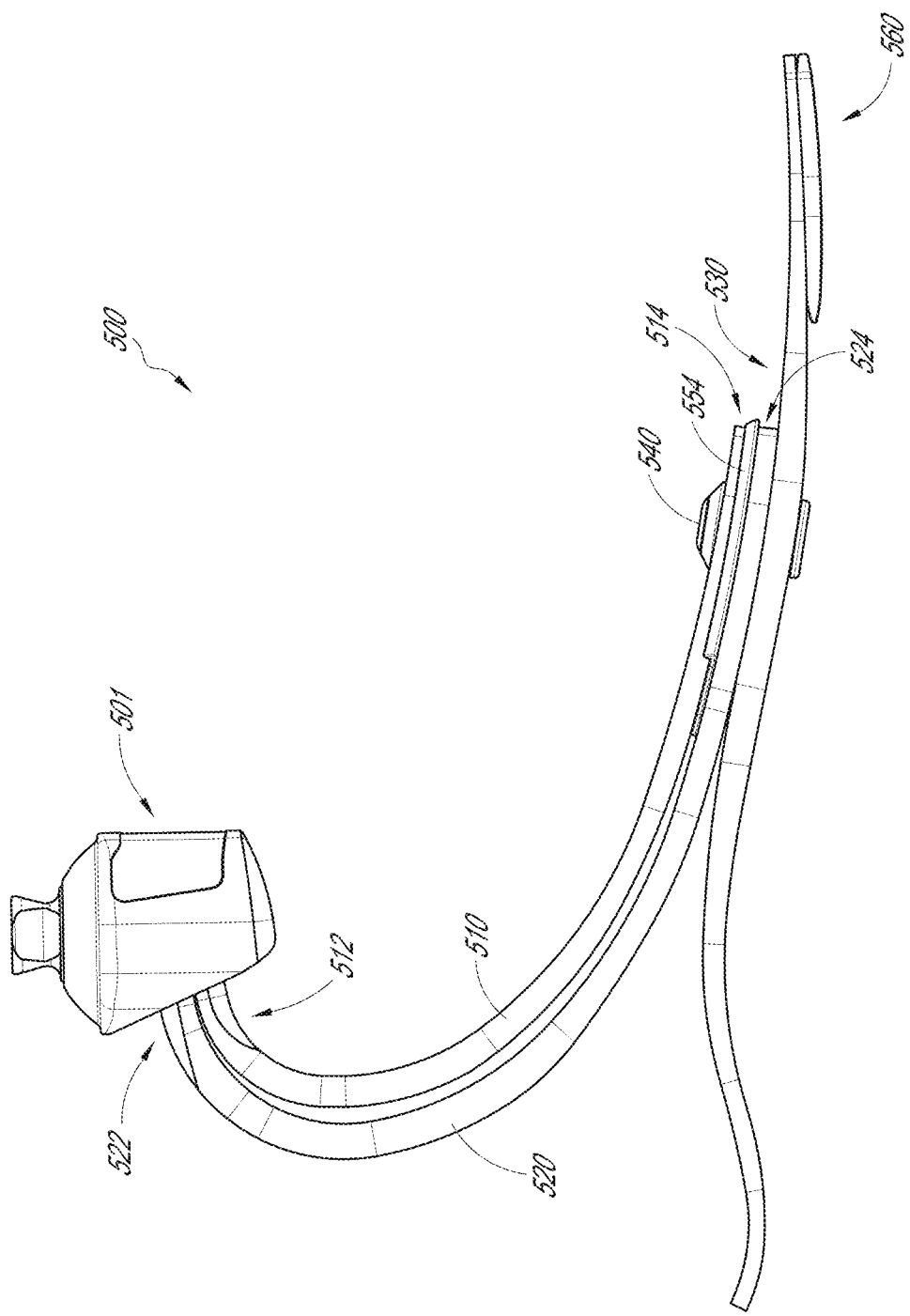
FIG. 4B is a side view of the prosthetic foot of FIG. 4A.

In other embodiments, a prosthetic foot can include material having variable stiffness properties disposed between portions of two foot elements along a partial length of the two foot elements. For example, FIGS. 3A-3F and 4A-4B illustrate examples of a prosthetic foot 500 including a material having variable stiffness properties disposed between distal portions of two foot elements. The prosthetic foot 500 in FIGS. 3A-3E can have an adapter 502 that is different than the adapter 501 in the prosthetic foot 500 in FIGS. 4A-4B (e.g., in size, shape, and the like). For example, the adapter 501 can be narrower than the adapter 502 when viewed from the side, such as shown in FIGS. 3B and 4B. The adapters 501, 502 can be used for coupling the prosthetic foot 500 to different types of interfaces, such as lower limb of a user, other prosthetic devices, and the like. The adapter 501 or the adapter 502 can be incorporated into the foot 100, 100'.

The prosthetic foot 500 can have any of features of the prosthetic foot 100, 100' except as described below. Accordingly, features of the prosthetic foot 500 can be incorporated into features of the prosthetic foot 100, 100' and features of the prosthetic foot 100, 100' can be incorporated into features of the prosthetic foot 500. Similar elements in the prosthetic foot 100 and the prosthetic foot 500 share numerical identifiers with the same last two digits.

Figure 5:
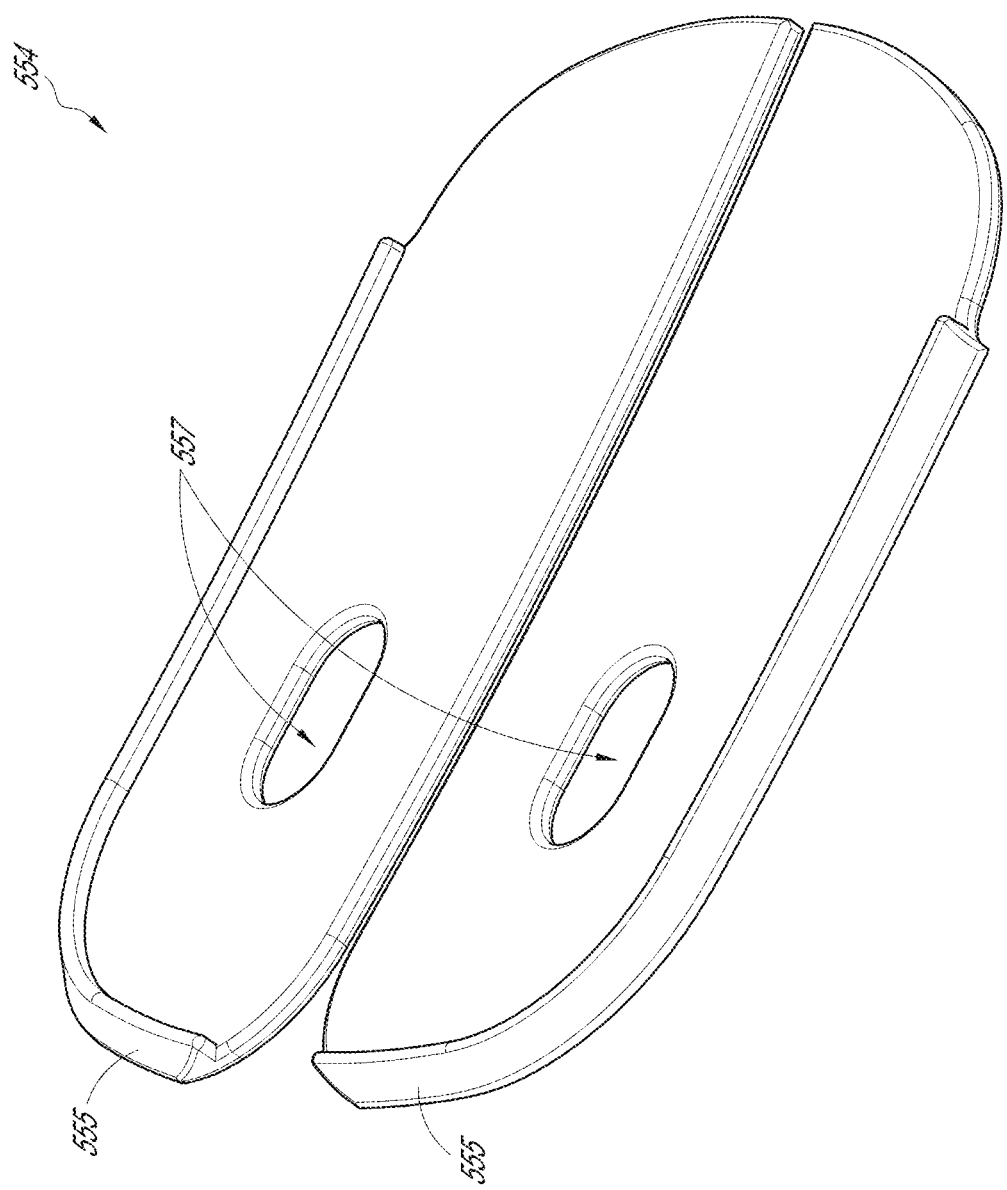
FIG. 5 is a perspective view of the material having variable stiffness properties in FIGS. 3A and 4A.

The gap between the upper foot elements 510, 520 can be partially filled with one or more layers 554. As shown in FIGS. 3A-3B and 4A-4B, one or more layers 554 of the above-described material that provides variable stiffness properties can fill a distal portion of the gap between the upper foot elements 510, 520, such as from the distal ends 514, 524 of the upper foot elements 510, 520 toward the proximal ends 512, 522 of the upper foot elements 510, 520. As shown in FIG. 5, the one or more layers 554 can include two pieces (e.g., two separate pieces, such as a lateral piece and a medial piece), which can be substantially mirror images of each other. The two pieces can be placed in the gap at the distal portion of the upper foot elements 510, 520 and be separated by a width at least substantially the same as the width of the split 516 in the upper foot elements 510. The upper foot element 520 can have a split in a similar location and/or of a similar shape as the slit 126 in FIG. 2C. In some embodiments, the two pieces can be joined (e.g., where the upper foot elements 510, 520 do not have splits). The one or more layers 554 of variable stiffness material can include a raised flange or lip 555 along a distal end and/or an outer edge (such as the lateral edge of the lateral piece and the medial edge of the medial piece) of the one or more layers 554. The raised flange or lip 555 can inhibit the one or more layers 554 of variable stiffness material from slipping proximally in the gap, advantageously helping to retain the one or more layers 554 in place during use of the prosthetic foot 500. The one or more layers 554 can include openings 557 near its distal end for accommodating the fasteners 540 that fasten the upper foot elements 510, 520, and the lower foot element 530.

Figure 6A:
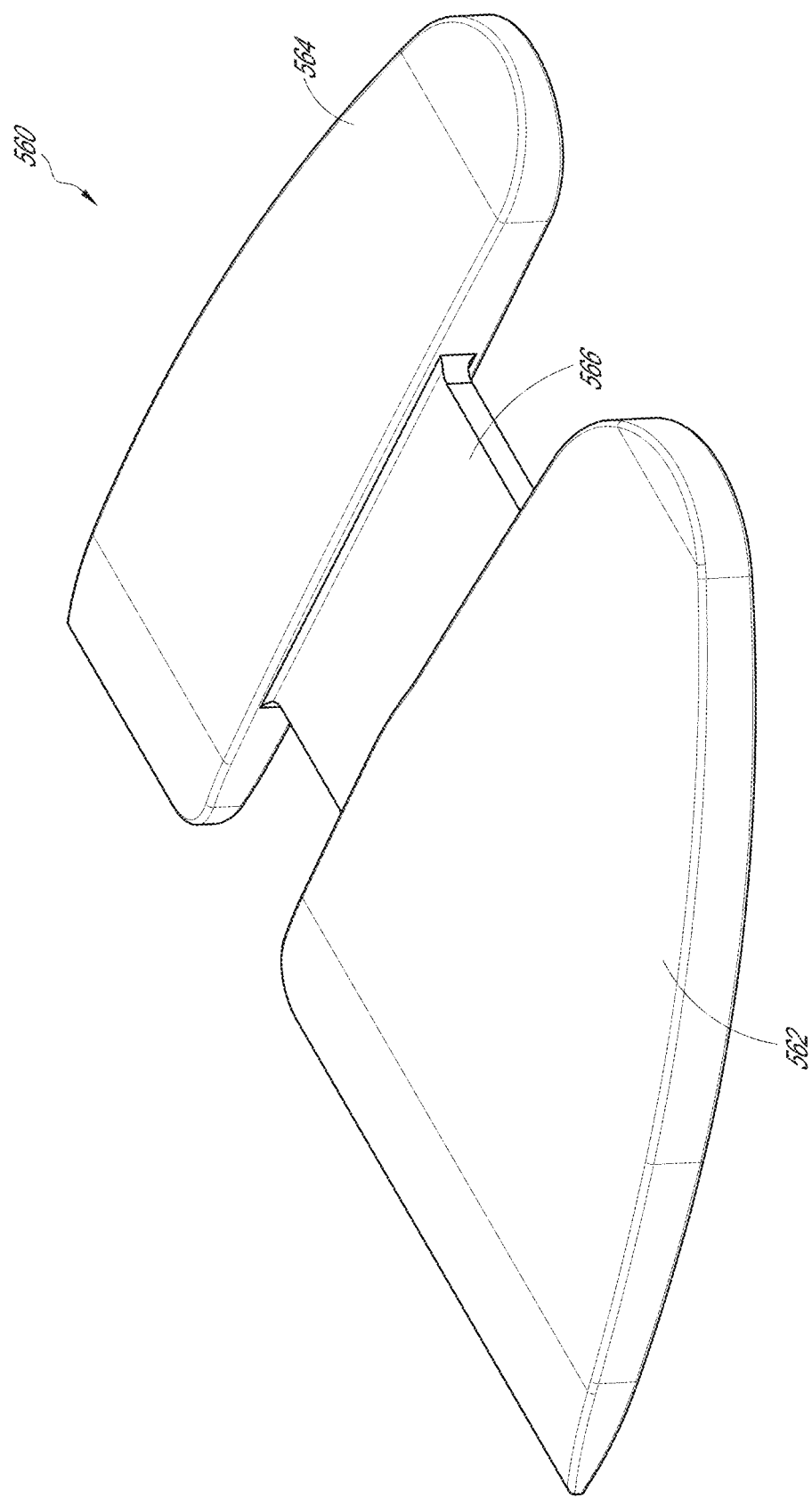
FIGS. 6A and 6B are perspective and front views of a toe pad in FIGS. 3A and 4A.
Figure 6B:
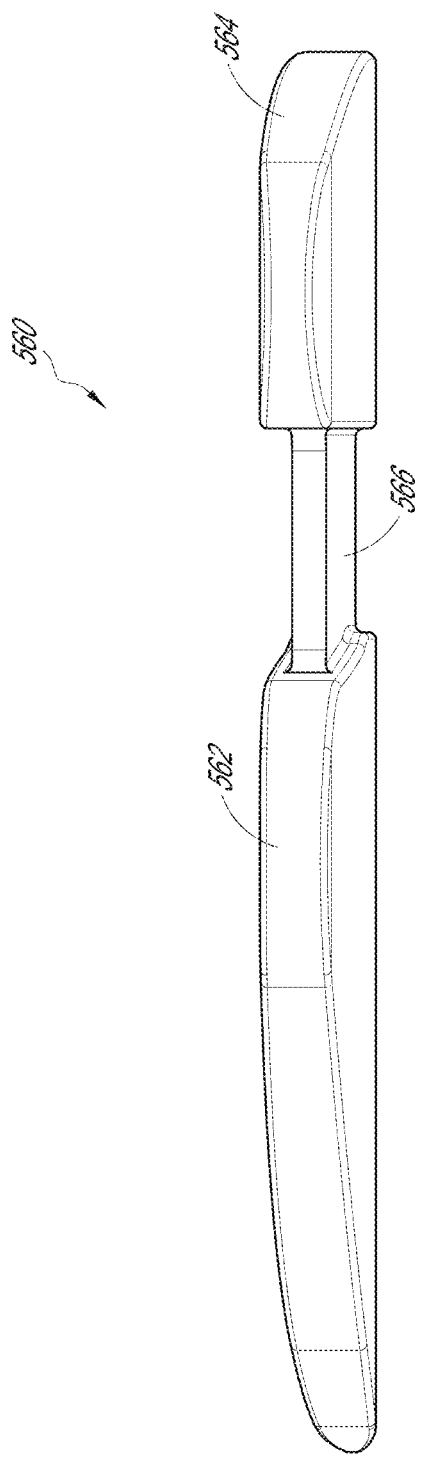

As shown in FIGS. 3A-3E, 4A-4B, and 6A-6B, the prosthetic foot 500 can include a toe pad 560 configured to be placed under the toe region of the lower foot element 530. As shown in FIG. 1, the foot 100 can also include a toe pad 160. In some embodiments, the toe pad 160 can have any of features of the toe pad 560. The toe pad 560 can be coupled to an underside of the lower foot element 530 using any suitable mechanisms, such as adhesives, magnets, screws, and the like. The toe pad 560 can include a lateral portion 562 and a medial portion 564. A shape and size of the lateral portion 562 and/or medial portion 564 can conform substantially to shapes and sizes of the medial and lateral portions of the lower foot element 530 at the toe region. As shown in the illustrated embodiments, the toe pad 560 can include a bridge 566 between the lateral portion 562 and the medial portion 564. As shown in FIGS. 6A and 6B, the bridge 566 can be thinner than a thickness of the lateral portion 562 and/or medial portion 564. The bridge 566 can be located across the U-shaped gap 537 of the lower foot element 530. In some embodiments, the bridge 566 may not contact a support surface (e.g., the ground) when the foot is resting on the support surface.

In some embodiments, the toe pad 560 can include separate lateral and medial portions, omitting the bridge. The toe pad 560 can optionally be made from a different material (e.g., more resilient, more flexible, more slip-resistant, or otherwise) than the lower foot element 530.

Figure 11:
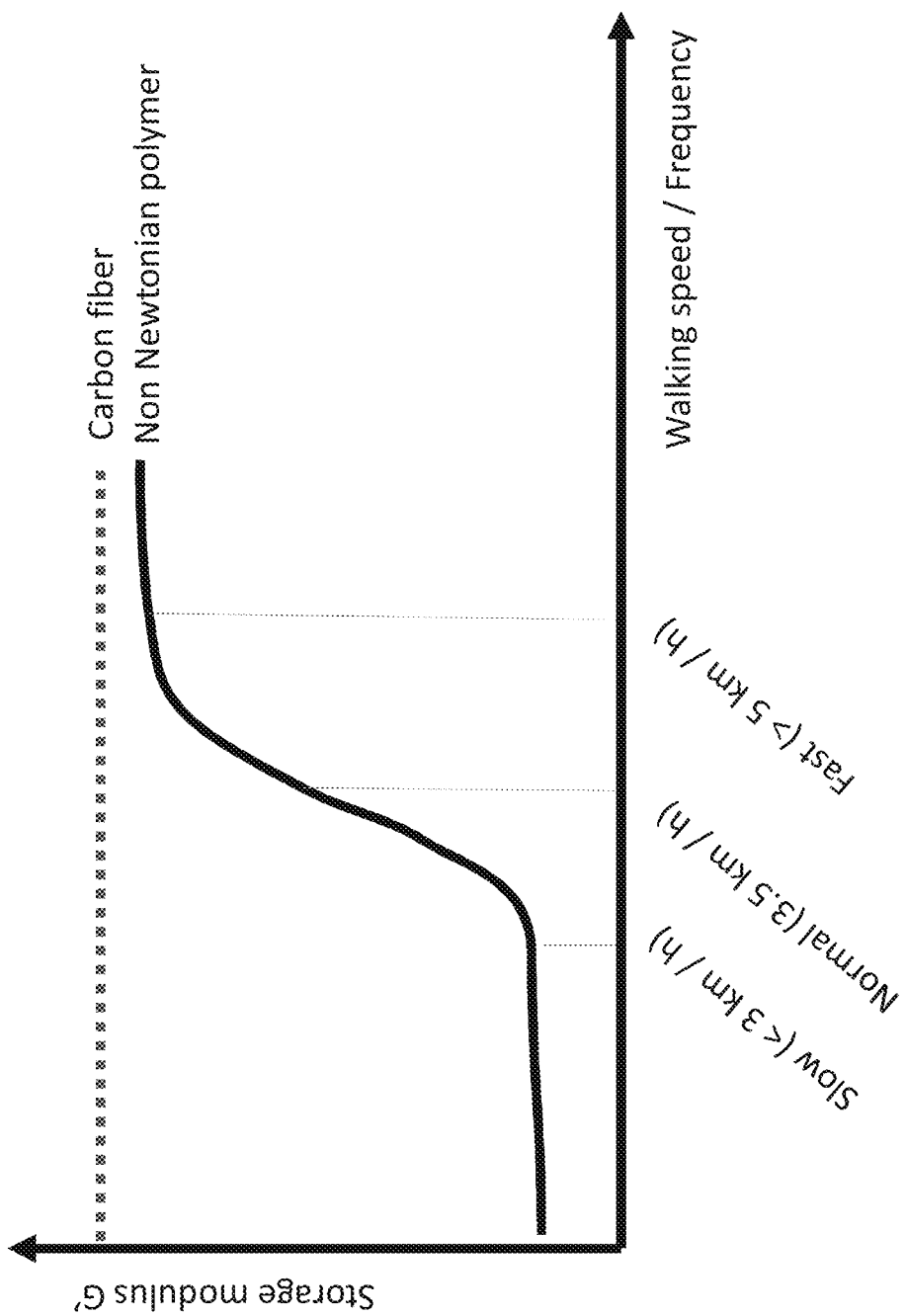
FIG. 11 is a graph of storage modulus G' vs. walking speed for a material having variable stiffness properties.

As the user walks on the prosthetic foot, the foot elements and one or more layers 150, 152, 554, compress and/or extend and experience shear forces. A speed dependent material (or another variable stiffness mechanism) can vary in compression and/or extension to adapt to various gait speeds, phases of the gait cycle, and/or activities. The speed dependent material or other variable stiffness mechanism can vary or act in compression and extension independently, with different characteristics in compression than in extension. The material compresses relatively faster at relatively higher walking speeds (e.g., greater than about 3 km/h) and relatively slower at relatively slower walking speeds (e.g., slower than about 3 km/h). The material selected preferably exhibits a relationship of storage modulus G' relative to temperature and/or frequency of impact (i.e., walking speed) as shown in the graph of FIG. 11. As also shown in FIG. 11, the storage modulus G' of carbon fiber remains the same, or substantially the same regardless of walking speed. As shown, the ideal material, when preset to ambient environmental temperature, exhibits a steep gradient change as walking speed increases from slow, e.g., less than about 3 km/h, to fast, e.g., greater than about 5 km/h. The material exhibits soft, high damped, less rebound foam-like behavior at slow walking speeds and stiffer, low damped and high rebound at fast walking speeds. The steep gradient change or steep slope of the graph means the material provides a significant change in stiffness when transitioning from slow to fast speeds (and vice versa).

The material can advantageously allow the prosthetic foot 100, 100', 500 to provide relatively high damping and energy absorption when the user is walking at relatively slow gait speeds and relatively high energy return and low damping when the user is walking at relatively faster walking speeds.

Figure 12:
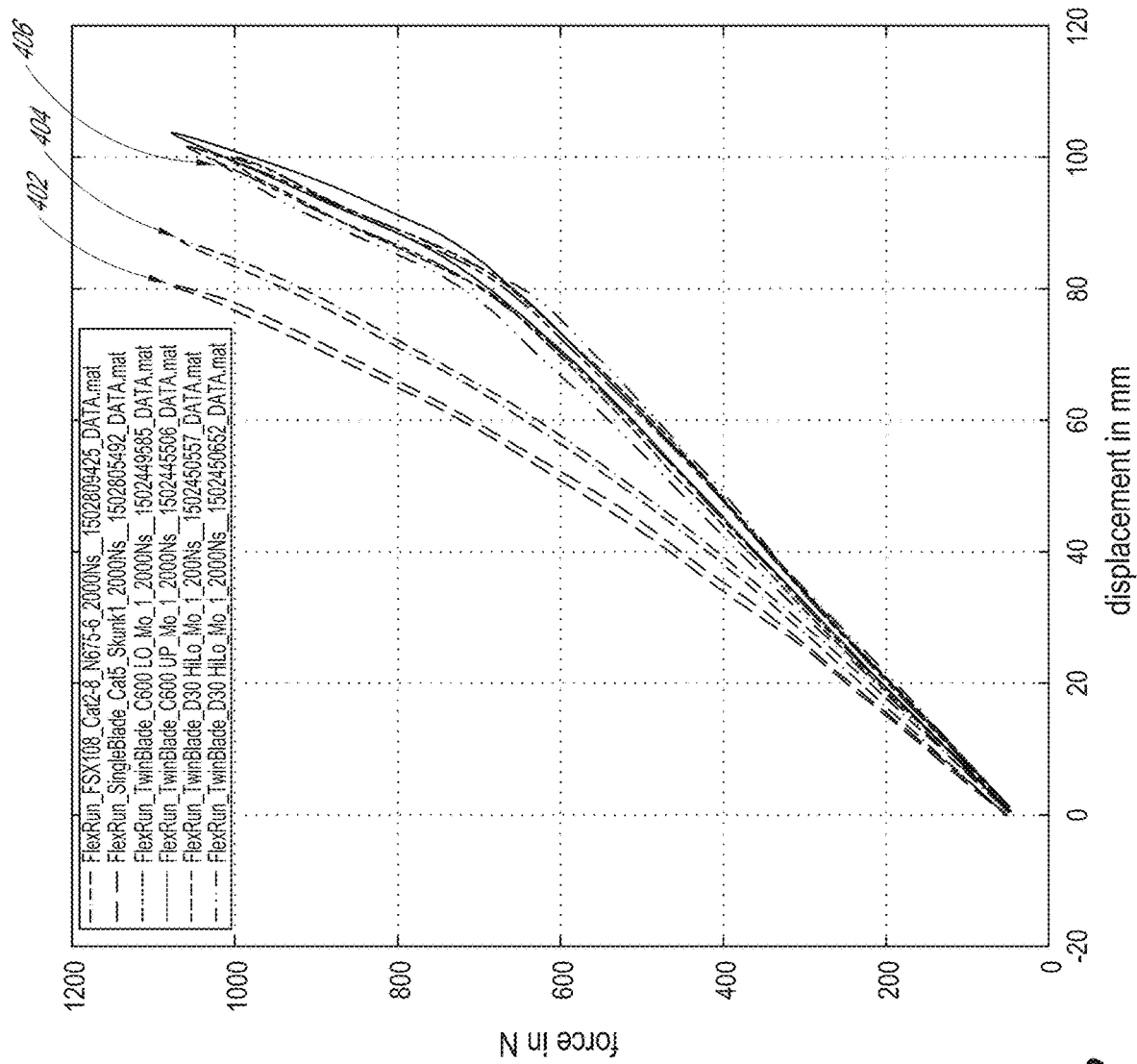
FIG. 12 is a graph of force vs. displacement for various prosthetic feet.
Figure 13:
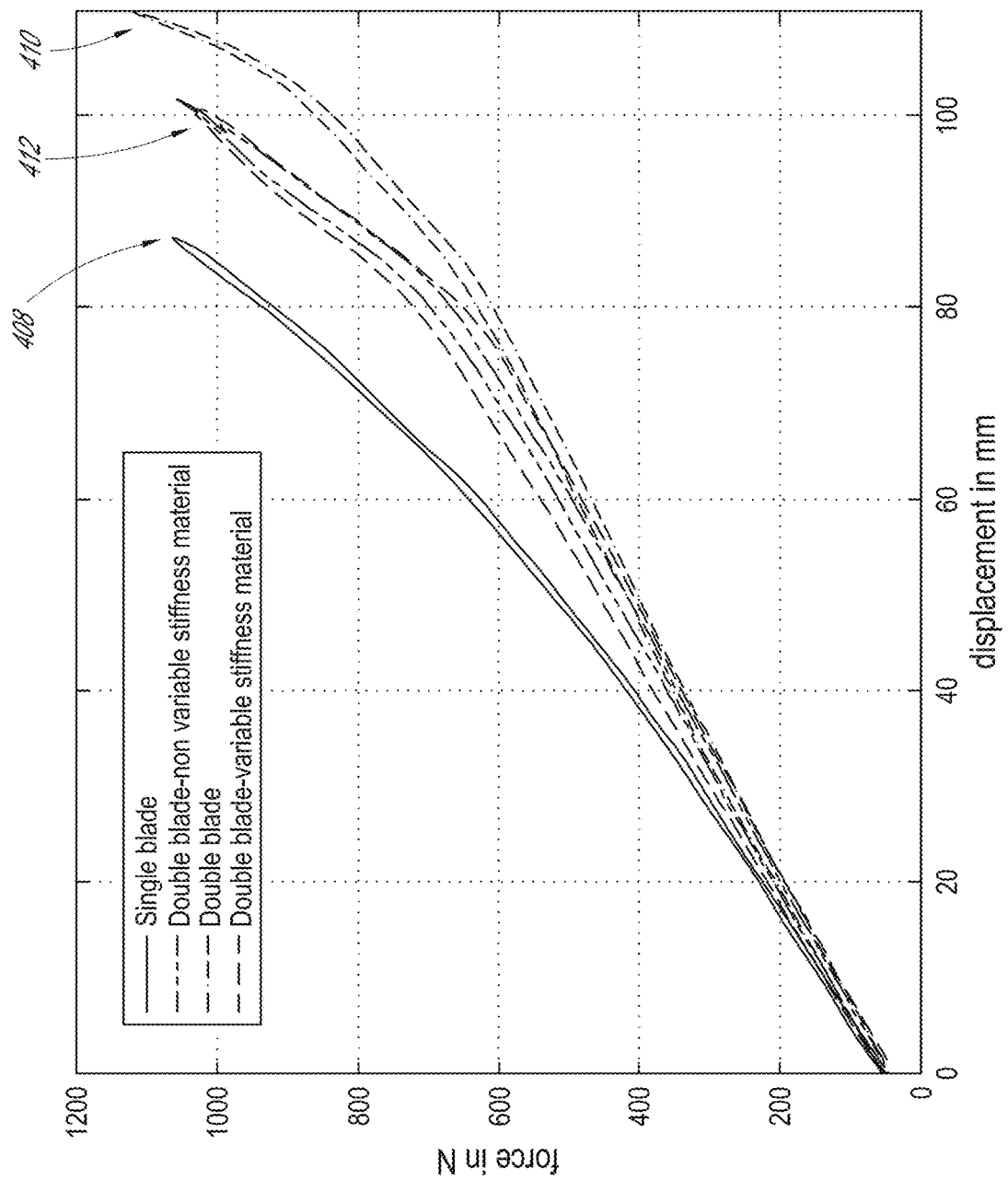
FIG. 13 is a graph of force vs. displacement for various prosthetic feet.

FIG. 12 shows a graph indicating the amount of displacement resulting from various levels of force for various prosthetic feet. Lines 402 show force vs. displacement for a prosthetic foot including a single foot element. Lines 404 show force vs. displacement for a prosthetic foot with a softer single foot element or spring. As shown, the softer foot element prosthetic foot exhibits greater displacement for a given amount of force compared to a less soft single foot element prosthetic foot. Lines 406 show force vs. displacement for a prosthetic foot including dual foot elements with a speed-dependent material disposed therebetween, as described herein. As shown, this prosthetic foot exhibits greater displacement for a given amount of force compared to the prosthetic feet with single foot elements. FIG. 13 illustrates force vs. displacement for a prosthetic foot including a single foot element (lines 408), a prosthetic foot including dual foot elements e.g., two separate pieces (lines 410), and a prosthetic foot including dual foot elements with one or more layers of a material disposed between the foot elements (lines 412). As shown, the prosthetic foot including dual foot elements with a material disposed therebetween exhibits, at least at greater force values (e.g., greater than around 600N), greater displacement for a given amount of force compared to a prosthetic foot including a single foot element, but less displacement for a given amount of force compared to a prosthetic foot including dual foot elements without a material disposed therebetween.

As shown in FIG. 12, there is a change (increase) in the slope of lines 406 at a force around or above 600 N, and the prosthetic foot exhibits less change in displacement for a given amount of increased force. In other words, at higher force levels (which correlate to faster walking speeds), the material disposed between the dual foot elements causes a stiffening effect of the prosthetic foot. FIG. 13 also shows a change (increase) in the slope of lines 412 at a force around or above 600N. At greater force values (e.g., greater than around 600N), the force vs. displacement lines 412 separate (at least to a greater extent) from lines 410. Including a material between dual foot elements therefore stiffens the prosthetic foot at faster walking speeds.

A variable stiffness mechanism, such as a material that exhibits variable stiffness properties as described herein, can also or alternatively be disposed at other locations of the prosthetic foot. For example, a variable stiffness mechanism can be disposed between upper foot element 120, 520 and the lower foot element 130, 530. Such a configuration can provide variable damping during heel strike. As another example, a variable stiffness mechanism can be used in a shock adapter, for example, coupled to the adapter 102, 501, 502, to provide variable vertical damping depending on the user's gait speed.

Other configurations of prosthetic feet and orthotic or limb support devices can include one or more layers 150, 152, 554 of the material that provides variable stiffness properties. For example, FIGS. 7A-7B, 8, and 9 illustrate another example embodiment of a prosthetic foot 200 including dual foot elements 210, 220. The prosthetic foot 200 does not include a lower foot element as in the embodiment of FIGS. 1, 2A-2D, 3A-3E, and 4A-4B. The foot elements 210, 220 are optionally made of a resilient, energy storing material, such as carbon fiber. The foot elements 210, 220 extend generally parallel to each other and have generally the same shape. In the illustrated embodiment, the foot elements 210, 220 are generally C-shaped. Other shapes are also possible (e.g., J-shape). The foot elements 210, 220 extend from proximal ends 212, 222 to distal or toe ends 214, 224. The foot elements 210, 220 can be the same or different lengths. The foot elements 210, 220 can be coupled to each other and/or an adapter, prosthetic pylon, the user's residual limb, or another prosthetic component proximate the proximal ends 212, 222. The foot elements 210, 220 can be coupled to each other proximate the distal ends 214, 224, for example, via fastener(s) (such as screw(s) or bolt(s)), adhesive(s), and/or other suitable mechanisms. In some embodiments, the foot elements 210, 220 can be coupled via fasteners extending through elongate holes, which can advantageously allow the foot elements 210, 220 to flex relatively more than if coupled via fasteners extending through round holes, for example, more closely matching the size and shape of the fasteners. The foot elements 210, 220 are separated by a gap along at least a portion of their lengths. The gap is at least partially filled with one or more layers 150 of a material that provides variable stiffness properties as discussed above. The one or more layers 150 of variable stiffness material can be connected to each other and/or to the foot elements 210, 220 via fasteners at or proximate the toe regions of the foot elements 210, 220. Additionally or alternatively, the one or more layers 150 of variable stiffness material can also be adhered (with an adhesive material) at the toe regions of the foot elements 210, 220.

Figure 10:
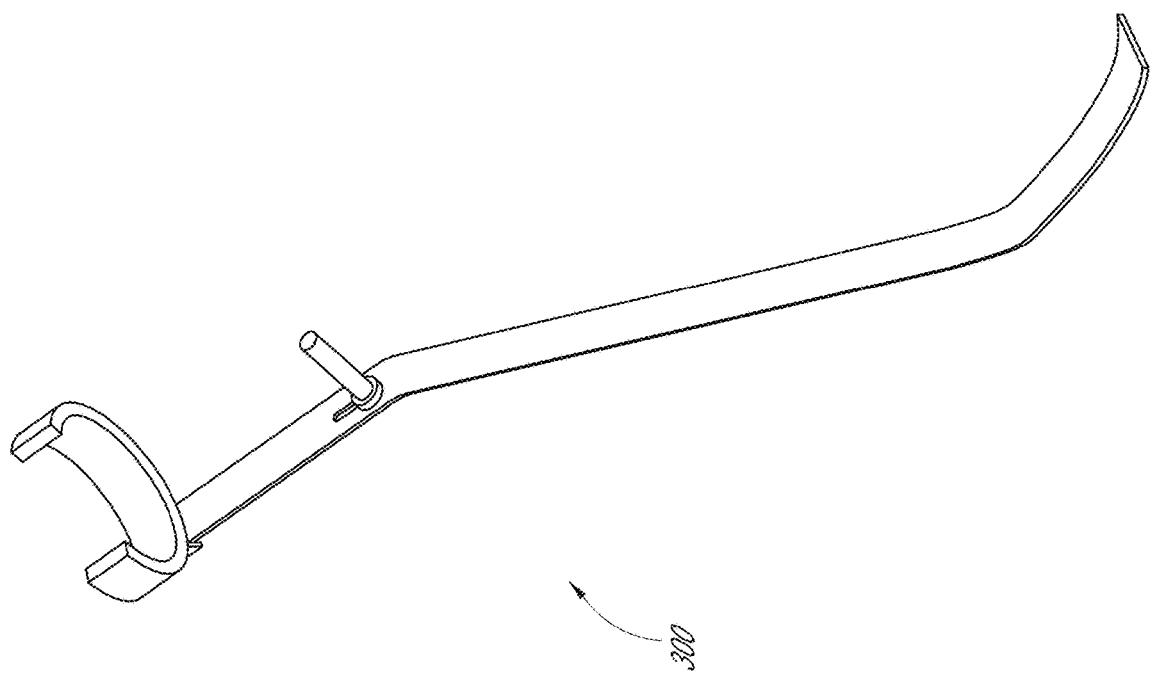
FIG. 10 is a front perspective view of an example embodiment of a crutch that can incorporate a material having variable stiffness properties.

As another example, FIG. 10 illustrates a crutch 300 used to support all or part of a user's body weight. The crutch 300 can be made of or include a resilient, energy storing material, such as carbon fiber. The crutch 300 can include dual blades extending along part or an entire length of the crutch 300. The dual blades can be separated by a gap along at least a portion of their lengths, and the gap can be at least partially filled with one or more layers 150, 152, 554 of a material that provides variable stiffness properties as discussed above.

Figure 7A:
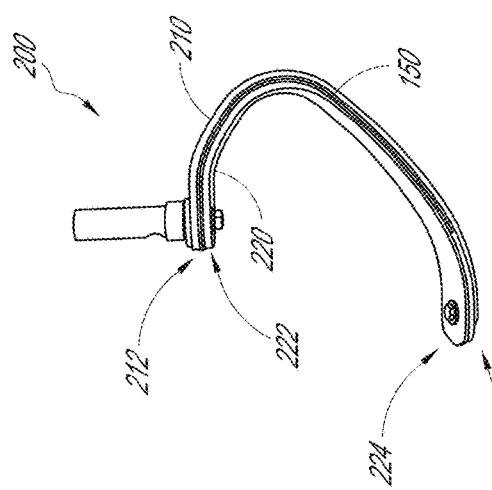
FIGS. 7A and 7B are side views of other example embodiments of a prosthetic foot including a material having variable stiffness properties disposed between two foot elements.
Figure 8:
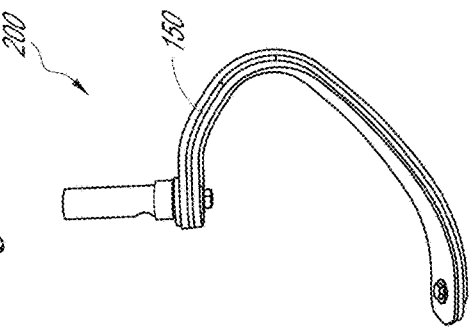
FIG. 8 is a side view of another example embodiment of a prosthetic foot including a material having variable stiffness properties disposed between two foot elements.
Figure 7B:
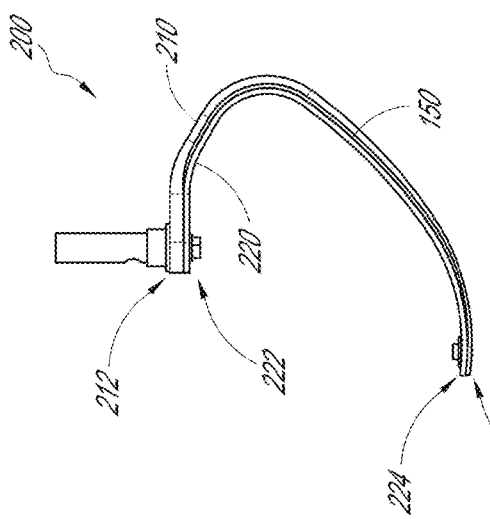
Figure 9:
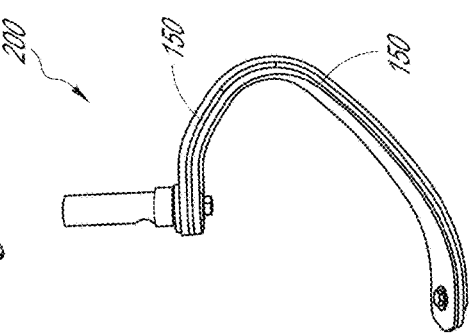
FIG. 9 is a side view of another example embodiment of a prosthetic foot including a material having variable stiffness properties disposed between two foot elements.

In any of the illustrated prosthetic feet or other configurations of prosthetic feet, the one or more layers 150, 152, 554 can extend along the entire length of the dual foot elements (e.g., 110, 120, 510, 520, or 210, 220) between which the layers 150, 152, 554 are disposed, as shown in FIGS. 1 and 2A. Alternatively, the one or more layers 150 can extend along only a portion of the length of the dual foot elements (e.g., 110, 120, 510, 500, or 210, 220), as shown in FIGS. 3A, 4A, 7A-7B and 9. In some embodiments, the portion(s) of the length of the dual foot elements including the one or more layers 150, 152, 554 are disposed at or include the proximal end of the prosthetic foot. In some such embodiments, the one or more layers 150, 152, 554 extend into or under the adapter 102, 502, 501 or prosthetic component to which the foot is coupled, e.g., a pylon as illustrated in FIGS. 7-9. In such a configuration, the one or more layers 150, 152, 554 can act as an initial impact absorber during gait. In some embodiments, the portion(s) of the length of the dual foot elements including the one or more layers 150, 152, 554 are disposed at or proximate or include the distal end or toe end or region of the foot. In some such embodiments, the one or more layers 150, 152, 554 are compressed by the clamping force of the fasteners coupling the dual foot elements together. The one or more layers 150 can be provided in a single continuous segment, as shown in FIGS. 1, 2A-2D, 3A-3E, 4A-4B and 9, or in two or more segments that may be separated from each other along the length of the dual foot elements, as shown in FIG. 8 (e.g., where layer sections 150 are separated by an open portion of the gap between the foot elements). The one or more layers 150, 152, 554 can have the same width and/or cross-sectional shape as the dual foot elements. Alternatively, the one or more layers 150, 152, 554 can have a different width, thickness, and/or cross-sectional shape than the dual foot elements. The one or more layers 150, 152, 554 can have a constant width, cross-sectional shape, and/or thickness along its length. Alternatively, the width, cross-sectional shape, and/or thickness of the one or more layers 150, 152, 554 can vary along its length.

In some embodiments, various characteristics of the one or more layers 150, 152, 554 (e.g., the material selected, thickness, cross-sectional shape, width relative to lateral edges of the foot elements, etc.) can differ between the medial and lateral sides of the prosthetic foot. This can allow for or encourage a more natural or biomechanical rollover (e.g., eversion and inversion) from heel strike to toe off during walking. The rollover can be further enhanced in embodiments including a slit that separate a foot element into medial and lateral blades. The enhanced rollover effect can be decreased at higher gait speeds allowing for less adaptation at higher speeds and more adaptation at slower speeds, as is biomechanically preferable.

The one or more layers 150, 152, 554 can optionally be secured, e.g. glued, laminated, and/or secured via fasteners such as bolts or screws, to one or both of the dual foot elements along a portion or an entire length of the dual foot elements. For example, the one or more layers of variable stiffness material can be connected via an adhesive material at the toe regions of the upper foot elements. In some embodiments, the foot elements can also be loosely connected via fasteners through elongate holes on the foot elements so that the foot elements can flex more than when the foot elements are connected via generally round holes.

In some embodiments, the one or more layers 150, 152, 554 can be secured to one or both of the dual foot elements proximate one or both longitudinal ends of the one or more layers 150, 152, 554, and a mid-portion along the length of the one or more layers 150 can be free moving or not secured to the dual foot elements. Adhesion among the foot elements and one or more layers 150, 152, 554 can cause the one or more layers 150, 152, 554 to act in extension as well as compression during use. This can increase the effect of speed-dependency. In some embodiments, the one or more layers 150, 152, 554 can have a wavy shape when viewed from the side to allow for higher compression ratios. Adhesion of the one or more layers 150, 152, 554 to the foot elements can increase the overall stiffness of the prosthetic foot. Adhesion of the one or more layers 150, 152, 554 to the foot elements can reduce shear forces among the one or more layers 150, 152, 554 and foot elements that could occur and cause wear on the prosthetic foot if, for example, the mid-portion along the length of the one or more layers 150, 152, 554 was free moving relative to the foot elements. In some embodiments, the one or more layers 150, 152, 554 can act in a shear direction. The one or more layers 150, 152, 554 can have a first end and a second end. The layers 150, 152, 554 can be secured at the first and second ends to the proximal 512, 522 and distal ends 514, 524 of the upper foot elements 510, 520 via bonding or clamping. In some embodiments, the bonding can be on at least one or both of the first and second ends. In one implementation, the one or more layers 150, 152, 554 may not be fixedly connected to the upper foot elements 510, 520.

The one or more layers 150, 152, 554 can be disposed between the dual foot elements during manufacturing, or post-manufacturing, for example, by a prosthetist. Instead of or in addition to the one or more layers 150, 152, 554 being disposed between the dual foot elements, the material can be intermixed with or directly inserted, laminated, or mixed into the carbon fiber material during manufacturing of the foot element(s). This can allow use of a single foot element in place of two foot elements with one or more layers 150, 152, 554 incorporated therein, which can advantageously reduce or eliminate certain wear effects that could result from shear forces between multiple layers.

The gap between the dual foot elements (e.g., 110, 120 or 210, 220) and/or the thickness of the one or more layers 150, 152, 554 can be selected such that when the prosthetic foot is at rest, the one or more layers 150, 152, 554 are not compressed. The thickness of the one or more layers 150, 152, 554 can be approximately the same as the thickness of the gap such that the one or more layers 150 are flush with both dual foot elements, and there is no space, or no significant space, between the one or more layers 150, 152, 554 and either of the dual foot elements. Alternatively, the thickness of the one or more layers 150, 152, 554 can be less than the thickness of the gap, such that there is space between the one or more layers 150, 152, 554 and one or both of the dual foot elements along a partial or entire length of the one or more layers 150, 152, 554. The gap between the dual foot elements and/or the thickness of the one or more layers 150, 152, 554 can be selected such that when the prosthetic foot is at rest, the one or more layers 150, 152, 554 are compressed (e.g., pre-compressed), for example, by 5-10%. The thickness of the one or more layers 150, 152, 554 can be constant or can vary over the length of the one or more layers 150, 152, 554.

Use of a speed-dependent material as described herein can advantageously allow the thickness of part or all of one or both of the dual foot elements to be reduced, such that the prosthetic foot 100, 100', 200, 500 can remain approximately the same weight with the one or more layers 150, 152, 554 as the prosthetic foot 100, 100', 200, 500 would be without the one or more layers 150, 152, 554 without the reduced foot element thickness. For example, the thickness of the foot element 110, 510 can be tapered or reduced toward the distal end 114, 514 such as shown in FIGS. 1, 3A, and 4A.

Though the variable stiffness mechanism is described above in connection with a prosthetic foot design, the variable stiffness mechanism can be incorporated into other prosthetic or orthotic devices to improve the gait performance of the device. For example, the variable stiffness mechanism can be incorporated into an ankle-foot orthosis (AFO) that can be utilized to support a user that suffers from a drop foot condition, or a knee-ankle-foot orthosis (KAFO) that can be utilized to support a user that suffers from pain, weakness or instability in their leg.

Conditional language used herein, such as, among others, "can," "could," "might," "may," "e.g.," and from the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it may be understood that various omissions, substitutions, and changes in the form and details of the ground contact sensing system, including the sensor components, logical blocks, modules, and processes illustrated may be made without departing from the spirit of the disclosure. As may be recognized, certain embodiments of the systems described herein may be embodied within a form that does not provide all of the features and benefits set forth herein, as some features may be used or practiced separately from others. Additionally, features described in connection with one embodiment can be incorporated into another of the disclosed embodiments, even if not expressly discussed herein, and the prosthetic device having the combination of features still fall within the scope of the invention. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A spring assembly comprising:
   a first elongate member extending along a length and made of a first material;
   a second elongate member extending generally parallel to the first elongate member along a length and made of the first material, the second elongate member separated from the first elongate member by a gap along at least a portion of its length; and
   one or more layers of a time-dependent second material disposed in the gap, wherein the one or more layers of the time-dependent material provide adjustable stiffness of the spring assembly at different rates of compression,
   wherein the spring assembly comprises a prosthetic foot.

2. The spring assembly of claim 1, wherein the second material is a non-Newtonian material.

3. The spring assembly of claim 1, wherein the first material is carbon fiber.

4. The spring assembly of claim 1, wherein the second material acts in one or both of compression and extension.

5. The spring assembly of claim 1, wherein the second material acts in compression and extension independently with different characteristics.

6. The spring assembly of claim 1, wherein stiff characteristics of the second material adjust automatically in compression and extension.

7. The spring assembly of claim 1, wherein the one or more layers have a wave shape configured to increase compression ratios of the one or more layers.

8. The spring assembly of claim 1, wherein the second material acts in a shear direction relative to one or both of the first and second elongate members.

9. A prosthetic foot comprising:
   a first elongate member extending along a length and made of a first material;
   a second elongate member extending generally parallel to the first elongate member along a length and made of the first material, the second elongate member separated from the first elongate member by a gap along at least a portion of its length; and
   one or more layers of a time-dependent second material having variable stiffness properties disposed in the gap,
   wherein the prosthetic foot exhibits greater energy absorption and damping characteristics at slower gait speeds and greater energy return and stiffer spring characteristics at faster gait speeds at least in part due to the one or more layers of the time-dependent second material.

10. The prosthetic foot of claim 9, wherein the slower gait speeds are less than about 3 km/h.

11. The prosthetic foot of claim 9, wherein the faster gait speeds are greater than about 5 km/h.

12. The prosthetic foot of claim 9, wherein a storage modulus G' of the second material decreases from the slower gait speeds to the faster gait speeds.

13. The prosthetic foot of claim 9, wherein the second material is a non-Newtonian material.

14. The prosthetic foot of claim 13, wherein the second material is an open or closed cell polyurethane.

15. The prosthetic foot of claim 9, wherein the first material is carbon fiber.

16. The prosthetic foot of claim 9, wherein the second material acts in one or both of compression and extension.

17. The prosthetic foot of claim 9, wherein the second material acts in compression and extension independently with different characteristics.

18. The prosthetic foot of claim 9, wherein stiff characteristics of the second material adjust automatically in compression and extension.

* * * * *